United States Patent [19]

Asanuma et al.

[11] Patent Number: 5,714,645
[45] Date of Patent: Feb. 3, 1998

[54] PROCESS FOR PRODUCING ALL TRANS-FORM POLYPRENOLS

[75] Inventors: Goro Asanuma, Okayama; Yoshin Tamai; Koichi Kanehira, both of Niigata, all of Japan

[73] Assignee: Kuraray Co., Ltd., Kurashiki, Japan

[21] Appl. No.: 739,287

[22] Filed: Oct. 29, 1996

[30] Foreign Application Priority Data

| Oct. 31, 1995 | [JP] | Japan | 7-308467 |
| Nov. 29, 1995 | [JP] | Japan | 7-334135 |
| Nov. 29, 1995 | [JP] | Japan | 7-334136 |

[51] Int. Cl.$^6$ ................................ C07C 33/02
[52] U.S. Cl. ......................... 568/875; 514/739
[58] Field of Search ............... 568/875; 514/739

[56] References Cited

U.S. PATENT DOCUMENTS

| 4,386,227 | 5/1983 | Sato | 568/875 |
| 4,668,820 | 5/1987 | Ibata | 560/248 |

FOREIGN PATENT DOCUMENTS 2 122 610  1/1984  United Kingdom.

OTHER PUBLICATIONS

Johnson, et al., "Olefinic Ketal Claisen Reaction. A Facile Route to Juvenile Hormone," Journal of the American Chemical Society, vol. 92, No. 14, Jul. 15, 1970, pp. 4463–4464.

Koptenkova, et al., "Synthesis of Prenols Omega–t$_2$c$_2$sOH Related to Dolichols," Bulletin of the Academy of Sciences of the USSR, Division of Chemical Science, vol. 36, No. 4, Pt. 2, Apr. 1987, pp. 743–747.

Veselovskii, et al., "Synthesis of Dolichol–Type (S)–Hexa–and (S)–Heptaprenols," Bulletin of the Academy of Sciences of the USSR, Division of Chemical Science, vol. 38, No. 9, Pt. 2, Sep. 1989, pp. 1887–1891.

Sato, et al., "General Method of Stereospecific Synthesis of Natural Polyprenols. Synthesis of Betulaprenol–6, –7, –8, and –9," Chemistry Letters, No. 7, Jul. 1984, pp. 1105–1108.

Sato, et al., "Stereospecific Synthesis of (Z,Z,Z,Z,Z,Z,Z,Z, E,E)–Undecaprenol (Bacterialprenol) Using an All–cis––Diterpene Buiding Block," Journal of the Chemical Society, Chemical Communications, No. 24, Dec. 15, 1986, pp. 1761–1762.

Poppe, et al., "Convenient Synthetic Route to (+)–Faranal and (+)–13–Norfaranal; The Trail Pheromone of Pharaoh's Ant and Its Congener," Tetrahedron, vol. 44, No. 5, 1988, pp. 1477–1487.

Chappe, "Synthesis of Three Acyclic All–trans–Tetraterpene Diols, Putative Precursors Bacterial Lipids", Bull Chem Soc Jpn. (61), pp. 141–148, Jan. 1988.

Sato, "Stereoselective Synthesis of Solanesol and all –trans––Decaprenol", J Chem Soc, Perkin Trans, (3) pp. 761–769, 1981.

Alonso, "Arene–catalysed Reductive Desulfonylation and Desulfinylation Reactions: New Routes for Alkyllithiums", Tetrahedron, vol. 51, No. 9 pp. 2699–2708, Feb. 1995.

Trost, "A New Approach for the Stereocontrolled Synthesis of Acyclic Terpenes", J Org Chem, vol. 40, No. 24, 1977, 1975.

Inoue, "Stereoselective Total Synthesis of (S)–(–)–Dolichol–20", J Chem Soc, Chem Commun, pp. 1036–1037, 1987.

Primary Examiner—C. Warren Ivy
Assistant Examiner—Jean F. Vollano
Attorney, Agent, or Firm—Oblon, Spivak, McClelland, Maier & Neustadt, P.C.

[57] ABSTRACT

An all trans-form polyprenol is obtained by;

(A) subjecting a 3,7-dimethyl-6-hydroxy-7-octen-1-ol derivative to five-carbon lengthening reaction m-times which comprises reacting with 2-methyl-3,3-dimethoxy-1-butene and reducing the carbonyl group of the resulting compound, to obtain an allyl alcohol derivative;

(B) halogenating the hydroxyl group of the allyl alcohol derivative to convert it to form an allyl halide derivative;

(C) allowing the allyl halide derivative to react with a polyisoprenyl sulfone derivative to form a sulfonated polyprenol derivative; and (D) subjecting the sulfonated polyprenol derivative to desulfonylation to obtain the all trans-form polyprenol.

9 Claims, No Drawings

PROCESS FOR PRODUCING ALL TRANS-FORM POLYPRENOLS

BACKGROUND OF THE INVENTION

1. Field of the Invention

This invention relates to all trans-form polyprenols such as 3,7,11,15,19,23,27-heptamethyl-6,10,14,18,22,26-octacosahexaen-1-ol (hereinafter "DHP").

2. Description of the Related Art

DHP is reported to be useful as a preventive or remedy for diseases caused by immunodeficiency of human beings or animals (Japanese Patent Application Laid-open No. 62-169724).

This DHP is a kind of polyprenols, and has a structural feature that the β- and γ-positions of the hydroxyl group are saturated and also all double bonds in the molecule are arranged in the trans form.

As a process for producing the DHP having such a structural feature, only a process as shown by Scheme 1 is known in the art (Japanese Patent Application Laid-open NO. 59-73533).

The process shown by scheme 1 is a process in which a starting material compound of Formula (10) is subjected to two-carbon lengthening reaction to obtain a DHP of Formula (1). Here, the starting material compound of Formula (10) can be synthesized by a process as shown by Scheme 2 [Isler et al., Helv. Chem. Acta., 42, p2616 (1959)].

Now, in Scheme 2, in order to obtain the compound of Formula (10), all double bonds of the starting material hexaprenol of Formula (20) must be arranged in the trans form. The hexaprenol having such a structure does not naturally occur and is not a starting material which is readily available.

Accordingly, it is considered that preferable is the production of the compound of Formula (10) using as a starting material a compound having a short prenyl unit, e.g., geraniol, which is readily available as a natural product or synthetic material. In this case, two routes are possible for its synthesis. One of them is a process in which carbon chains are successively lengthened by partly utilizing the process shown by Scheme 2 to synthesize the compound of Formula (10) as shown by Scheme 3. The other is a process in which as key reactions the reaction to oxidize geranyl acetate of Formula (40) in the presence of selenium dioxide and the coupling reaction in the presence of butyl lithium are utilized to synthesize the hexaprenol of Formula (20) as shown by Scheme 4, the product being used as the starting material for the process of Scheme 2 [J. Chem. Soc. Perkin Trans. I, p761 (1981)].

SCHEME 1

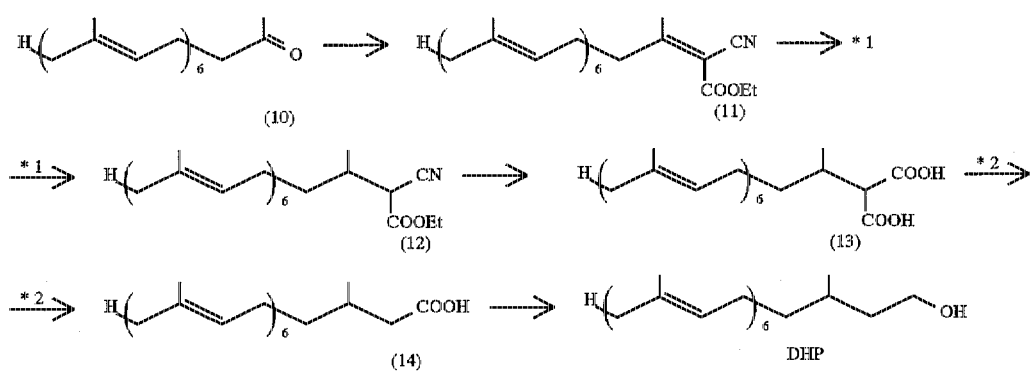

SCHEME 2

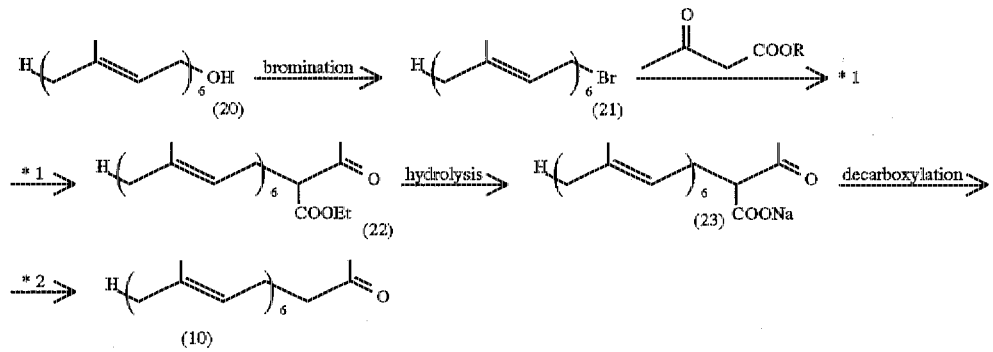

SCHEME 3
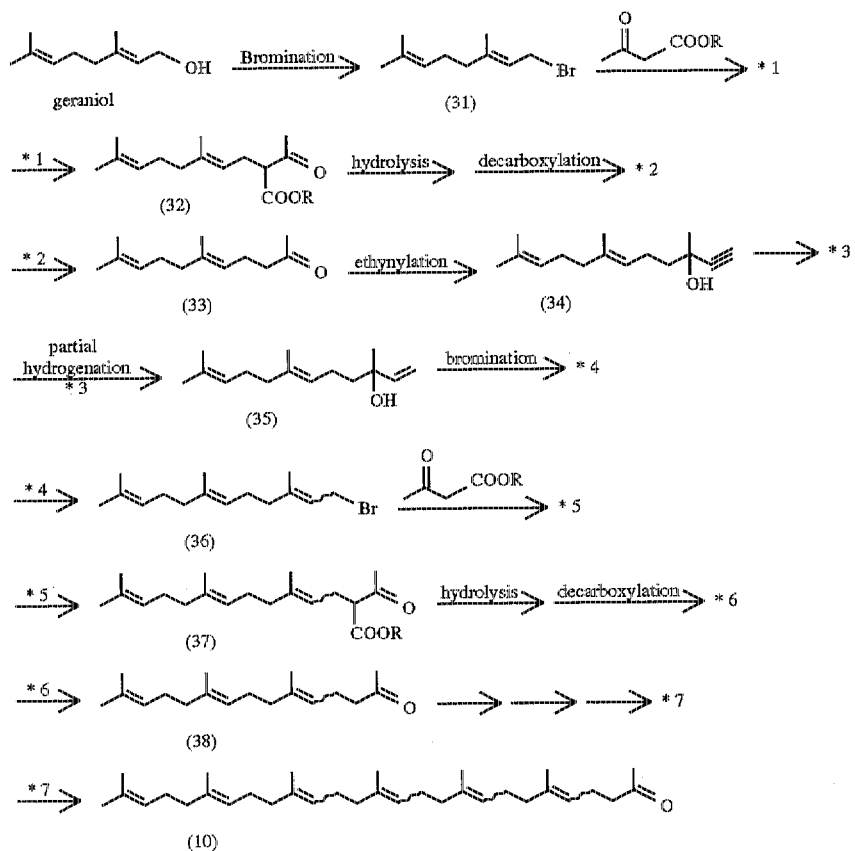
SCHEME 4
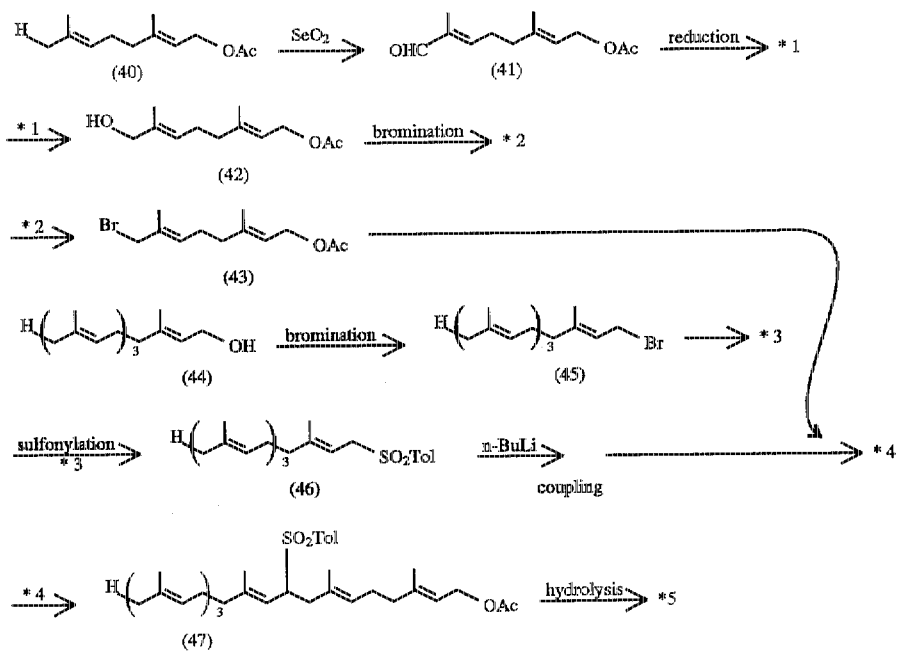

-continued
SCHEME 4

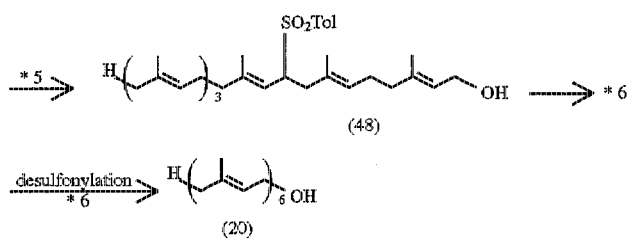

In the case of the process shown by Scheme 3, however, six steps are required in order to carry out the five-carbon lengthening reaction corresponding to one prenyl unit [from the compound of Formula (33) to the compound of Formula (38)], so that twenty or more steps are required in order to finally obtain the compound of Formula (10) from the geraniol, resulting in a complicated operation for the synthesis and also a low total yield to leave a problem. Moreover, in the step of converting the compound of Formula (35) to the compound of Formula (36), there is the problem that the double bonds at the β- and γ-positions of the bromine group also form cis-type isomers as by-products. Consequently, the yield of compounds in which all double bonds are arranged in the trans form is very low when the compound of Formula (10) is produced by the process of Scheme 3. Taking account of the present level of techniques, it is also very difficult to separate and obtain the compound of Formula (10) from a mixture with isomers in which the double bonds are arranged in the cis form, in a good efficiency and in an industrial scale.

As for the case of the process shown by Scheme 4, a harmful selenium dioxide is used at the step where the compound of Formula (41) is obtained, and also the yield of the compound is as low as 44%. In addition, the reaction to desulfonylate the compound of Formula (48) is carried out under reaction conditions of a very low temperature of −78° C., and there is the problem that the reaction can be carried out with difficulty in an industrial scale. Accordingly, as the desulfonylation reaction, one may contemplate to carry out reducing desulfonylation reaction on the compound of Formula (47) by the use of lithium, a commonly available metal. In such a case, however, there is the problem that even though a protective group is introduced the alcohol competitively causes elimination reaction to form the compound of Formula (51) as a by-product as shown by Scheme 5.

SCHEME 5

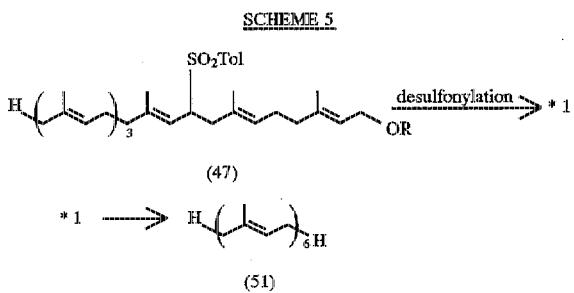

Thus, it is difficult to produce the compound of Formula (10), the starting material for producing the DHP, at a low cost and in a good efficiency by utilizing the process of Scheme 3 or 4.

As the process for producing the DHP, another process is possible in which the double bonds at the β- and γ-positions of an alcohol are selectively hydrogenated in part directly from a corresponding polyprenyl alcohol. Such hydrogenation, however, commonly has so poor regioselectivity that even other double bonds not intended to be reduced are hydrogenated in excess, and consequently it is difficult to selectively obtain only the DHP.

In relation to processes for producing the DHP, it is also sought to develop an industrially advantageous process for producing compounds in which all double bonds in the molecule are arranged in the trans form, which are polyprenols useful as starting materials for a coenzyme $Q_{10}$ or β,γ-dihydropolyprenols useful as preventives or remedies for diseases caused by immunodeficiency of human beings or animals. Correspondingly thereto, it is also sought to make it possible to produce in an industrially advantageous manner an allyl halide derivative of the (poly)prenol serving as a starting material for their synthesis, and also to carry out in an industrially advantageous manner the desulfonylation reaction utilized when polyprenols are produced, as will be detailed below.

That is, as a process commonly used to synthesize polyprenols, a process is known in which, as shown by Scheme 6, a compound of Formula (113) obtained from an allyl sulfone compound of Formula (111) and an allyl halide compound of Formula (112) is desulfonylated.

SCHEME 6

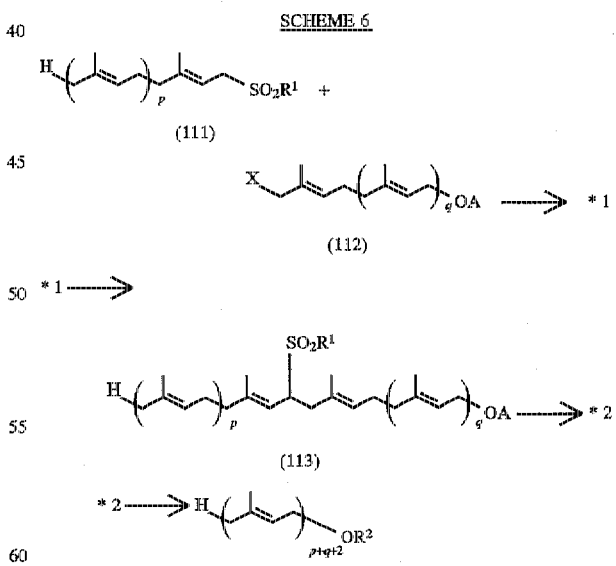

In the above formulas, p and q represent an integer of 0 or 1 or more. $R^1$ represents an alkyl group or an aryl group, and A represents a protective group of the hydroxyl group. X represents a halogen atom, and $R^2$ represents a hydrogen atom or the same protective group of the hydroxyl group as that of A.

The synthesis process shown by Scheme 6 is a synthesis process in which a long polyprenyl chain is constructed by combination of compounds having short prenyl chains. This is a synthesis process advantageous for synthesizing polyprenols having a long chain. Such a synthesis process is a process that is applicable also to the synthesis of a β,γ-dihydropolyprenol obtained by hydrogenating the β- and γ-positions of the hydroxyl group of the polyprenol.

As processes for synthesizing the above allyl halide compound of Formula (112) in Scheme 6, the following processes are known in the art. (I) A process in which the hydroxyl group of a corresponding polyprenol is protected to form a compound of Formula (120), which is thereafter oxidized in the presence of selenium dioxide to convert it to a compound of Formula (121) having an aldehyde group at the terminal, subsequently the aldehyde group is reduced with a metal hydride such as sodium borohydride, and the alcohol of Formula (122) thus produced is halogenated using a halogenating agent such as thionyl chloride or phosphorus tribromide (see Scheme 7) [Sato et al., J. Chem. Soc. Perkin Trans. I, p761 (1981)].

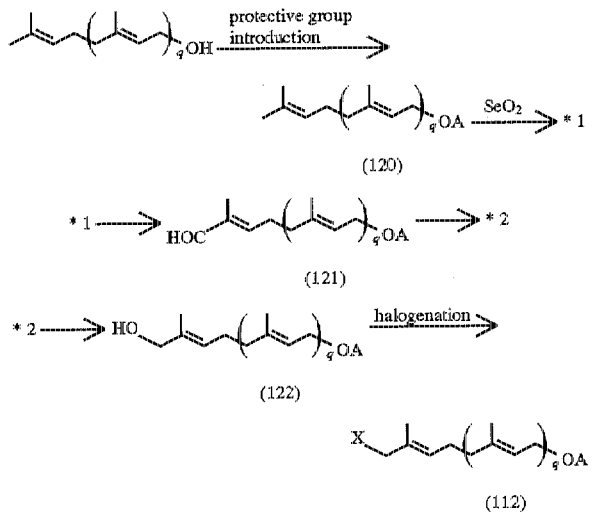

(II) A process in which the hydroxyl group of the polyprenol is protected to form a compound of Formula (120), which is thereafter reacted with hydrochlorous acid, N-chloroacetamide or N-bromosuccinimide to convert it to a halohydrine of Formula (123), which is subsequently ring-closed with a base to obtain an epoxy compound of Formula (124), and the epoxy compound of Formula (124) thus obtained is hydrolyzed to lead it to a diol compound of Formula (125), which is further subjected to dehydration reaction, and the secondary allyl alcohol of Formula (126) thus obtained is halogenated (see Scheme 8) (see Japanese Patent Application Laid-open No. 53-84908).

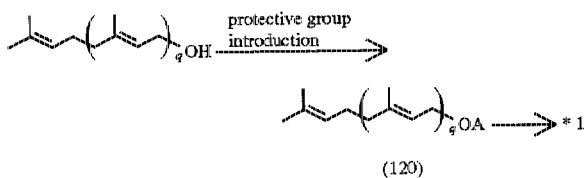

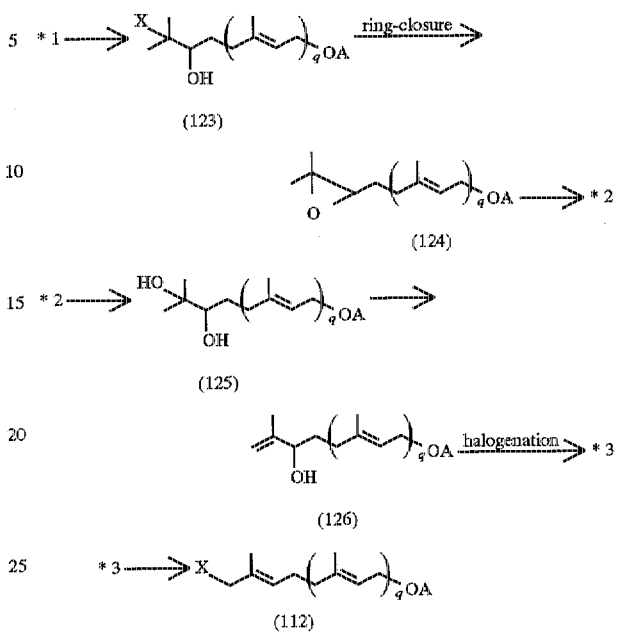

(III) In relation to the above process (II), a process is also known in which the compound of Formula (120) obtained by protecting the hydroxyl group of the polyprenol is oxidized with peracetic acid to obtain the epoxy compound of Formula (124), followed by rearrangement reaction to lead it to the secondary allyl alcohol of Formula (126) [see Terao et al., Synthesis, p467 (1979)].

In the process described in the above (I), however, harmful selenium dioxide is used and also the yield of the desired compound can not be said to be high. The process (I) also causes a decrease in selectivity of reaction with an increase in the chain length of the starting material polyprenol.

As for the process described in the above (II), it is a multi-stepwise reaction, resulting in a low yield of the ally halide compound of Formula (112). The starting material polyprenol is not available at a low cost when it has a large chain length, in particular, when q is 2 or more.

Combination of the process (II) with the process described in the above (III) makes it possible to decrease the number of reaction steps for synthesizing the allyl halide compound of Formula (112). However, when q is two or more, the selectivity to the terminal double bond at the time of epoxidation is so low that a mixture with an isomer different in the position of the epoxy group is obtained. As the result, the desired allyl halide compound of Formula (112) can not be selectively obtained.

Thus, it is difficult to say that the production of the allyl halide compound of Formula (112) using the process described in the above (I) or (II) is industrially advantageous.

Hence, when the polyprenol is to be produced in an industrial scale according to the process shown by Scheme 6, it is a technical subject to establish a process for producing selectively and in an industrially advantageous manner the synthesis intermediate allyl halide compound of Formula (112), in particular, the one in which q is 2 or more.

The synthesis process shown by Scheme 6 is, as previously stated, a synthesis process in which a long polyprenyl chain is constructed by combination of compounds having short prenyl chains. This can be said to be a synthesis process advantageous for synthesizing polyprenols having a long chain. Such a synthesis process is a process that is applicable also to the synthesis of a β,γ-dihydropolyprenol obtained by saturating the double bonds at the β- and γ-positions of the hydroxyl group of the polyprenol.

As methods for desulfonylation in Scheme 6, the following methods are known in the art.

(a) A method in which the compound of Formula (113) is reacted with metallic sodium in ethanol or tetrahydrofuran [see Yamazaki et al., Chem. Parm. Bull., Vol. 32, p3959 (1984)].

(b) A method in which the compound of Formula (113) is reacted with sodium amalgam [see Sato et al., J. Chem. Soc. Perkin Trans. I, p761 (1981)].

(c) A method in which the compound of Formula (113) is reacted with an alkali metal such as metallic lithium or metallic sodium in ammonia or a lower alkylamine such as anhydrous methylamine or anhydrous ethylamine (what is called Birch reduction) [see Sato et al., J. Chem. Soc. Perkin Trans. I, p761 (1981) and Japanese Patent Application Laid-open No. 53-84908].

(d) A method in which the compound of Formula (113) is reacted with a metal hydride or an organic metal hydride in the presence of a palladium catalyst [see Inomata et al., Chem. Lett., p1177 (1986).

When the polyprenol in which all double bonds in the molecule are arranged in the trans form is to be produced by the process shown by Scheme 6, it becomes necessary not only to carry out desulfonylation in a good efficiency but also to stereoselectively and regioselectively construct the double bonds.

When, however, the desulfonylation method shown in the above (a) is employed at the time of the desulfonylation in Scheme 6, it is necessary to use metallic sodium and alcohol in great excess, and besides the reaction product obtained contains 30% of double-bond position isomer, leaving the problem of a low selectivity.

In the desulfonylation method of the above (b), too, the reaction product obtained contains 30% of double-bond position isomer, leaving the problem of a low selectivity. Moreover, a waste containing mercury is produced, and there is a possibility of causing environmental pollution.

As for the desulfonylation method of the above (c), which utilizes Birch reduction, the desired compound can be obtained in a selectivity of as good as 90%, but it is necessary to use ammonia or lower alkylamine, having a low-boiling point. Moreover, in order to improve the selectivity of reaction, it is necessary to carry out the reaction at very low temperature. Such very low-temperature reaction is a reaction that can be carried out with difficulty in an industrial scale. Also, in general, the lower alkylamine, having a low boiling point, can be recovered with difficulty in an anhydrous state, and hence has a difficulty in respect of the recovery and reuse of solvents.

In addition, the method of the above (d), which makes use of a metal hydride or an organic metal hydride, the selectivity of reaction is as good as 95%, but lithium triethylborohydride is expensive and also expensive palladium catalyst must be used together. Hence, this method can not be said to be advantageous when carried out in an industrial scale.

Hence, when the polyprenol in which all double bonds in the molecule are arranged in the trans form is to be produced selectively and in an industrial scale by utilizing the process shown by Scheme 6, it is a technical subject to establish suitable conditions for the desulfonylation.

SUMMARY OF THE INVENTION

An object of the present invention is to provide a process by which all trans-form polyprenols such as DHP can be produced at a low cost, in a good efficiency and in an industrial scale.

Another object of the present invention is to provide a process by which allyl halide derivatives of polyisoprenol can be produced in an industrially advantageous manner.

Still another object of the present invention is to provide a process by which desulfonylation reaction can be carried out in an industrially advantageous manner to produce polyisoprenol.

That is, according to a first embodiment, the present invention provides a process for producing a all trans-form polyprenol represented by Formula (1):

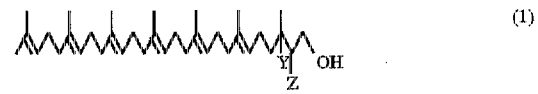

wherein Y and Z each represent a hydrogen atom, or combine to form a carbon-carbon bond; the process comprising the steps of:

(A) subjecting a compound represented by Formula (2):

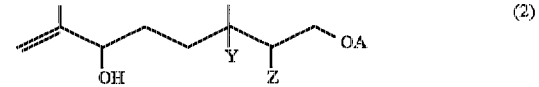

wherein Y and Z are as defined above, and A represents a protective group of the hydroxyl group; to five-carbon lengthening reaction m-times which comprises reacting the compound of Formula (2) with 2-methyl-3,3-dimethyoxy-1-butene and reducing the carbonyl group of the resulting compound to obtain a compound represented by Formula (3):

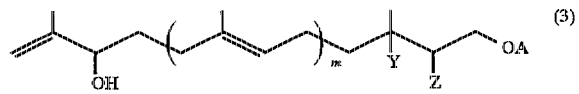

wherein Y, Z and A are as defined above, and m represents an integer of 1 to 4;

(B) subjecting the compound represented by Formula (3), to halogenation to convert it to a compound represented by Formula (4):

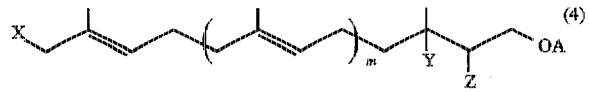

wherein Y, Z and A are as defined above, and X represents a halogen atom;

(C) allowing the compound represented by Formula (4) to react with a compound represented by Formula (5):

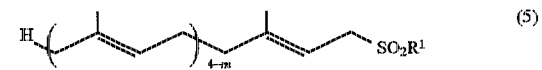

wherein m is as defined above, and $R^1$ represents an alkyl group or an aryl group; to obtain a compound represented by Formula (6):

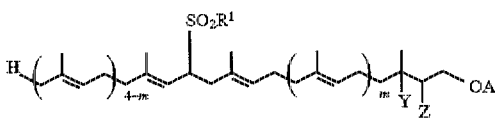

(6)

wherein Y, Z, A, m and $R^1$ are as defined above; and (D) subjecting the compound represented by Formula (6) to desulfonylation and deprotection to obtain the all trans-form polyprenol represented by Formula (1).

According to a second embodiment, the present invention provides a process for producing a compound represented by Formula (101):

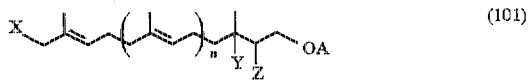

(101)

wherein X represents a halogen atom; Y and Z each represent a hydrogen atom, or combine to form a carbon-carbon bond; A represents a protective group of the hydroxyl group; and n represents an integer of 1 or more;

the process comprising the steps of:

(A') subjecting a compound represented by Formula (2):

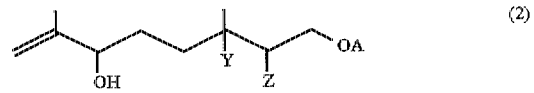

(2)

wherein Y, Z and A are as defined above; to five-carbon lengthening reaction n-times which comprises reacting the compound of Formula (2) with 2-methyl-3,3-dimethoxy-1-butene and reducing the carbonyl group of the resulting compound, to obtain a compound represented by Formula (103):

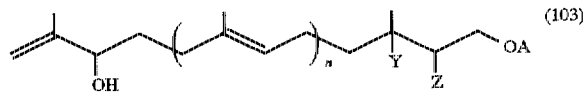

(103)

wherein Y, Z, A and n are as defined above; and (B') subjecting the compound represented by Formula (103), to halogenation to obtain the compound represented by Formula (101).

According to a third embodiment, the present invention provides a process comprising treating a compound represented by Formula (202):

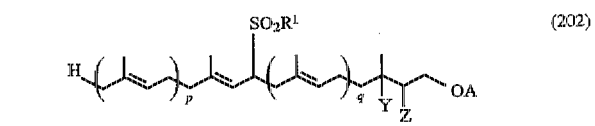

(202)

wherein p and q each represent an integer of 0 or 1 or more; Y and Z each represent a hydrogen atom, or combine to form a carbon-carbon bond; $R^1$ represents an alkyl group or an aryl group; and A represents a protective group of the hydroxyl group;

with an alkali metal and a polycyclic aromatic compound to produce a compound represented by Formula (201):

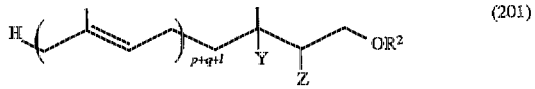

(201)

wherein p, q, Y and Z are as defined above; and $R^2$ represents a hydrogen atom or the same protective group of the hydroxyl group as that represented by A.

DETAILED DESCRIPTION OF THE INVENTION

First, the production process according to the first embodiment of the present invention will be described in detail for each step.

Step (A)

In the present invention, the compound of Formula (2) is subjected to five-carbon lengthening reaction m-times (here, m is an integer of 1 to 4) which comprises reacting the compound of Formula (2) with 2-methyl-3,3-dimethoxy-1-butene and reducing the carbonyl group of the resulting compound, to obtain the compound of Formula (3).

In this step, the protective group for the hydroxyl group, represented by A in Formula (2), may include known protective groups used for the purpose of protecting alcohols, and may include, e.g., an acetyl group, a tetrahydropyranyl group, a benzyl group and a t-butyldimethylsilyl group. In particular, a benzyl group is preferred, which is simultaneously feasible for deprotection at the time of desulfonylation in the step D described later.

The five-carbon lengthening reaction in this step will be described in greater detail with reference to Scheme 9.

SCHEME 9

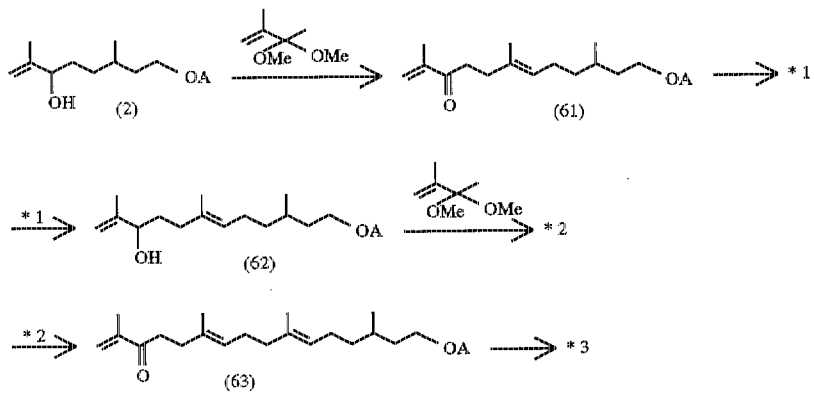

-continued
SCHEME 9

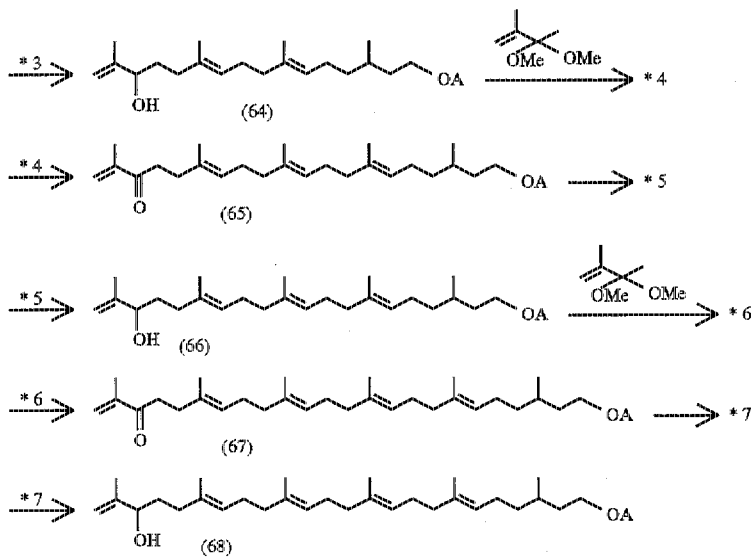

As shown in Scheme 9, in the five-carbon lengthening reaction in this step, the compound of Formula (2) is first allowed to react with 2-methyl-3,3-dimethoxy-1-butene to obtain a compound of Formula (61). Next, the the carbonyl group of the compound of Formula (61) is reduced to convert it to a compound of Formula (62). This compound of Formula (62) corresponds to the compound of Formula (3) in which m is 1.

Next, the compound of Formula (62) thus obtained is subjected to the same five-carbon lengthening reaction as in the case of the compound of Formula (2) to obtain a compound of Formula (64), which corresponds to the compound of Formula (3) in which m is 2.

On the compound of Formula (64) obtained, further similar five-carbon lengthening reaction is repeated to obtain a compound of Formula (66), which corresponds to the compound of Formula (3) in which m is 3, and further a compound of Formula (68), which corresponds to the compound of Formula (3) in which m is 4.

Here, the 2-methyl-3,3-dimethoxy-1-butene used in this five-carbon lengthening reaction is a known compound, and can be readily synthesized by, e.g., the method described in J. Am. Chem. Soc., 92, p4663 (1970).

With regard to the amount of the 2-methyl-3,3-dimethoxy-1-butene used, based on the amount of the compound of Formula (2), Formula (62), Formula (64) or Formula (66) (hereinafter "substrate"), the former may preferably be used in a molar equivalent weight of from 1 to 10, and more preferably in a molar equivalent weight of from 1.1 to 1.5, based on the substrate.

In the reaction of the substrate with the 2-methyl-3,3-dimethoxy-1-butene, an acid catalyst may preferably be used. As the acid catalyst, a variety of mineral acids or organic acids commonly used may be used, including, e.g., concentrated sulfuric acid, phosphoric acid and p-toluenesulfonic acid. In particular, pyridinium salts of p-toluenesulfonic acid may preferably be used. The acid catalyst may be used usually in an amount of from 0.01 to 10% by weight, and preferably from 0.05 to 1% by weight, based on the weight of the substrate.

In the reaction of the substrate with the 2-methyl-3,3-dimethoxy-1-butene, it is preferable to use a solvent. As the solvent, aromatic solvents such as benzene, toluene and xylene may preferably be used. In particular, toluene may preferably be used. The solvent may preferably be used in an amount of from 0.5 to 20 times by weight, and more preferably from 2 to 8 times by weight, based on the weight of the substrate.

In the reaction of the substrate with the 2-methyl-3,3-dimethoxy-1-butene, the reaction may be carried out at a temperature of usually from 50° to 150° C., and preferably from 80° to 110° C., and for a time of usually from 1 to 5 hours.

In the reaction of the substrate with the 2-methyl-3,3-dimethoxy-1-butene, methanol is produced with the progress of reaction. Accordingly, in order to allow the reaction to proceed in a good efficiency, it is preferable to carry out the reaction while distilling outside the system the methanol being produced.

The compounds of Formula (61), Formula (63), Formula (65) and Formula (67) can be reduced by known methods. For example, these compounds can be reduced to the compounds of Formula (62), Formula (64), Formula (66) and Formula (68), respectively, in high yields by Meerwein-Ponndorf reduction which uses a secondary alcohol and an aluminum alkoxide.

Here, the Meerwein-Ponndorf reduction may also be carried out after the compound to be reduced is separated and obtained by a conventional method, from a reaction mixture of the reaction of the substrate with the 2-methyl-3,3-dimethoxy-1-butene. From the viewpoints of the yield of the desired compound and the simplification of operation, the reaction mixture may preferably be subjected to the reduction reaction as it is.

The secondary alcohol used in this reduction reaction may include, e.g., isopropanol and 2-butanol. In particular, isopropanol is preferred.

The secondary alcohol may preferably be used in an amount of 1 to 10 times by weight, and more preferably from 2 to 6 times by weight, based on the weight of the compound of Formula (61), Formula (63), Formula (65) or Formula (67).

The aluminum alkoxide may include, e.g., aluminum ethoxide, aluminum isopropoxide and aluminum 2-butoxide.

The aluminum alkoxide may preferably be used in an amount of from 1 to 100 mol%, and more preferably from 5 to 40 mol%, based on the compound of Formula (61), Formula (63), Formula (65) or Formula (67).

The reduction reaction may be carried out at a temperature within the range of usually from 50° to 150° C., and preferably from 80° to 110° C.

Acetone is produced with the progress of reduction reaction. Accordingly, in order to allow the reaction to proceed in a good efficiency, it is preferable to carry out the reaction while distilling the acetone outside the system.

After the reaction is completed, an aqueous acid solution such as dilute hydrochloric acid or dilute sulfuric acid is added to the reaction mixture in an amount that is in excess with respect to the aluminum alkoxide used in the reaction, to thereby decompose the aluminum alkoxide, and the organic layer obtained is separated. This organic layer is treated by a conventional method to obtain the compound of Formula (3).

The double bonds newly formed as a result of the above five-carbon lengthening reaction come to be arranged in the trans form by 95% or more. Hence, even when the five-carbon lengthening reaction is repeatedly carried out, the proportion of the by-product cis isomers can be controlled to a very low level.

The compound of Formula (2) can be produced according to the following steps (a), (b) and (c) as shown by Scheme 10, and can be produced from citronellol, which is readily available, in the case when Y and Z are hydrogen atoms, or from geraniol, which is also readily available, in the case when Y and Z combine to form a carbon-carbon bond [Japanese Patent Application Laid-open No. 53-84908; Synthesis, p467 (1979)].

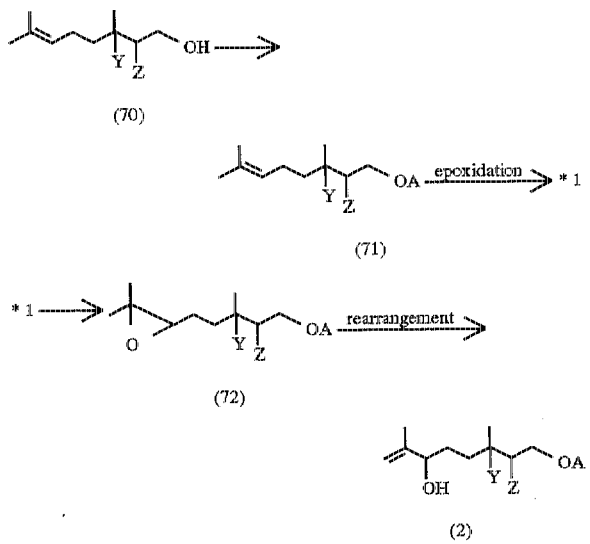

Step (a)

First, a compound of Formula (70) is converted to a compound of Formula (71) by introducing a protective group A into the hydroxyl group.

Here, the protective group A may be introduced by a method appropriately selected from any known methods in accordance with protective groups, e.g., by the method described in a publication "Green, Protective Groups in Organic Synthesis, 2nd Edition, John Wiley & Sons (1991)". For example, when a benzyl group is introduced as the protective group, a benzyl halide such as benzyl chloride or benzyl bromide may be allowed to react with the compound of Formula (70) (citronellol or geraniol) in the presence of a phase transfer catalyst in an aqueous solution of an alkali compound including alkali metal hydroxides such as sodium hydroxide and potassium hydroxide. This is advantageous from an economical viewpoint.

In this instance, the alkali compound in the aqueous alkaline solution may preferably be in a concentration of from 40 to 50% by weight. The alkali compound may be used in a molar equivalent weight of from 1 to 10, and more preferably in a molar equivalent weight of from 3 to 5, based on the compound of Formula (70). The benzyl halide can be enough when used in an amount which is in slight excess with respect to the the compound of Formula (70) in terms of molar equivalent weight.

As the phase transfer catalyst, for example, quaternary ammonium salts such as tetrabutylammonium chloride, tetrabutylammonium bromide and tetrabutylammonium sulfate may preferably be used. There are no particular limitations on the amount of the phase transfer catalyst used. Usually, it may be set to an amount that provides a concentration within the range of from 0.01 to 1 mol % based on the reaction mixture.

The reaction temperature may be set within the range of from 0° to 100° C., and preferably from 40° to 60° C. The reaction time may usually be within the range of from 1 to 10 hours.

After the reaction is completed, the reaction mixture is subjected to extraction with an organic solvent such as hexane, toluene or isopropyl ether, followed by treatment for separation by a conventional method to obtain the compound of Formula (71).

Step (b)

Next, the compound of Formula (71) is converted to a compound of Formula (72).

The compound of Formula (71) may be allowed to react with hypochlorous acid, N-chloroacetamide, N-bromosuccinimide or the like to form a halohydrin derivative, followed by reaction with a base to effect ring closure to thereby obtain the compound of Formula (72).

In the case when Y and Z are hydrogen atoms in Formula (71), the compound of Formula (71) in which Y and Z are hydrogen atoms [hereinafter referred to "the compound of Formula (71-1)"] is allowed to react with an epoxidizing agent to convert it to the compound of Formula (72) in which Y and Z are hydrogen atoms [hereinafter referred to "the compound of Formula (72-1)"].

Here, as the epoxidizing agent, for example, organic peroxides such as metachloroperbenzoic acid, monoperphtalic acid and t-butylhydroperoxide, peroxides such as hydrogen peroxide, and air may be used. In view of industrial easiness to handle, t-butylhydroperoxide may preferably be used. As the t-butylhydroperoxide, what is commercialy available as an aqueous 70% solution or a toluene solution may preferably be used.

The epoxidizing agent can be enough when used in an amount which is in slight excess with respect to the compound of Formula (71-1) in terms of molar equivalent weight.

In the epoxidation, it is preferable to use a metal catalyst such as molybdenyl acetylacetonate or vanadium oxide as a catalyst for accelerating the reaction. Such a metal catalyst may preferably be used in an amount of from 0.01 to 10% by weight, and more preferably from 0.05 to 1% by weight, based on the weight of the compound of Formula (71-1), which may be appropriately adjusted taking account of the reaction time and reaction selectivity.

In the epoxidation, it is preferable to use a solvent. As the solvent, aromatic solvents such as benzene, and toluene may preferably be used. In particular, toluene is preferred. Such a solvent may preferably be used in an amount of from 0.5 to 10 times by weight, and more preferably from 2.0 to 5 times by weight, based on the weight of the compound of Formula (71-1).

The epoxidation may be carried out at a reaction temperature of usually from 50° to 150° C., and preferably from 70° to 100° C. The reaction time may vary depending on the type and amount of the solvent, the reaction temperature and the type and amount of the catalyst used, and may usually be from 1 to 20 hours.

After the reaction is completed, the reaction mixture is subjected to decomposition of an excess epoxidizing agent using a reducing agent such as hydrosulfite or sodium sulfite, and thereafter to extraction with an organic solvent such as hexane, toluene or diisopropyl ether, followed by treatment for separation by a conventional method to obtain the compound of Formula (72-1).

Step (c)

Next, with regard to the compound of Formula (72), its epoxy group is rearranged to an allyl alcohol to convert it to the compound of Formula (2).

Here, the rearrangement reaction may be carried out under known conditions. For example, it can be carried out in a high yield by heat-refluxing the compound in toluene in the presence of aluminum isopropoxide as a catalyst [see Synthesis, p467(1979)].

Through the foregoing steps (a) to (c), the compound of Formula (2) can be obtained in a good efficiency in an industrial scale.

Step (B)

The compound of Formula (3) obtained in Step (A) is halogenized to convert it to the compound of Formula (4). The halogen atom represented by X in Formula (4) may include a chlorine atom and a bromine atom.

It can be halogenized by any conventional methods of converting alcohols to halides. For example, it can be done by allowing a halogenating agent such as thionyl chloride to react with the compound of Formula (3) in a solvent such as isopropyl ether, according to the method described in Japanese Patent Application Laid-open No. 54-76507. The compound of Formula (4) can be thereby obtained in a high yield.

The halogenating agent may preferably be used in a molar equivalent weight of from 0.9 to 2, and more preferably in a molar equivalent weight of from 1.0 to 1.8, based on the compound of Formula (3). There are no particular limitations on the amount of the solvent used, and the solvent may be used usually in an amount of from 0.5 to 5 times by weight based on the compound of Formula (3). The halogenation may be carried out at a temperature of usually from −20° to 50° C., and for a time of usually from 0.5 to 24 hours.

Step (C)

Next, the compound of Formula (4) obtained in Step (B) is allowed to react with the compound of Formula (5) to obtain the compound of Formula (6).

In the compound of Formula (5), the alkyl group represented by $R^1$ may preferably include lower alkyl groups such as a methyl group, an ethyl group and a butyl group. The aryl group may preferably include aromatic hydrocarbons such as a phenyl group, a tolyl group and a naphthyl group. These alkyl groups or aryl groups may be substituted with a variety of substituents so long as they do not adversely affect the reaction.

The reaction of the compound of Formula (4) with the compound of Formula (5) may be carried out according to known reaction conditions. For example, a base such as sodium methylate, sodium t-butoxide or potassium t-butoxide may be reacted in an aprotic polar solvent such as dimethylformamide, dimethyl sulfoxide, dimethyl imidazolidinone or N-methylpyrrolidone. The compound of Formula (6) can be thereby obtained in a high yield.

The base may preferably be used in a molar equivalent weight of from 0.8 to 4, and more preferably in a molar equivalent weight of from 1.0 to 2, based on the compound of Formula (5).

The compound of Formula (5) may preferably be used in a molar equivalent weight of from 0.5 to 2, and more preferably in a molar equivalent weight of from 0.8 to 1.2, based on the compound of Formula (4).

There are no particular limitations on the amount of the aprotic polar solvent used, and the solvent may be used usually in an amount of from 0.5 to 10 times by weight based on the compound of Formula (4).

The reaction may be carried out at a temperature of usually from −20° to 50° C., and for a time of usually from 1 to 24 hours.

The compound of Formula (5) is a known compound, and can be obtained by, e.g., brominating a corresponding polyprenyl alcohol with phosphorus tribromide, followed by reaction with a sulfinate such as sodium benzenesulfinate or sodium toluenesulfinate, according to the method described in J. Chem. Soc. Perkin Trans. I, p761(1981). Stated specifically, compounds of Formula (5) in which m is 4, 3, 2 and 1 can be obtained from prenol, geraniol, farnesol and geranyl geraniol, respectively, which are readily available.

Step (D)

The compound of Formula (6) obtained in Step (C) is subjected to desulfonylation and also deprotection to convert it to the compound of Formula (1). Here, the desulfonylation and the deprotection may be successively carried out in the manner divided in two steps. From an industrial viewpoint, it is preferable to carry out the desulfonylation and the deprotection simultaneously under appropriate selection of the protective group.

The desulfonylation (and deprotection) of the compound of Formula (6) may be carried out by known desulfonylation methods as exemplified by a method in which the compound of Formula (6) is reacted with an alkali metal in alcohol, a method in which the compound of Formula (6) is reacted with an alkali metal in a lower alkylamine (what is called Birch reduction), a method in which the compound of Formula (6) is reacted with a metal hydride, a method in which the compound of Formula (6) is reacted with an amalgam of an alkali metal, a method in which the compound of Formula (6) is reacted with an alkali metal and a polycyclic aromatic compound. In particular, it is preferable to carry out the desulfonylation by the use of an alkali metal and a polycyclic aromatic compound.

As the alkali metal, for example, lithium, sodium and potassium may be used. As the polycyclic aromatic compound, naphthalene, anthrathene, biphenyl and the like may be used. From the viewpoint of economical advantage and easiness to handle, it is preferable to use sodium as the alkali metal and naphthalene as the polycyclic aromatic compound.

When the alkali metal and the polycyclic aromatic compound are used in the desulfonylation reaction, the both may each be added alone in the reaction system, or may be added after, e.g., sodium metal is dispersed in molten naphthalene followed by solidification to form a complex such as a sodium-naphthalene complex.

The alkali metal may preferably be used in a molar equivalent weight of from 4 to 20, and more preferably in a molar equivalent weight of from 5 to 10, based on the compound of Formula (6). Also, the polycyclic aromatic compound may preferably be used in a molar equivalent weight of from 4 to 20, and more preferably in a molar equivalent weight of from 5 to 10, based on the compound of Formula (6).

The desulfonylation (and deprotection) may preferably be carried out in the presence of a solvent. As the solvent, ether type solvents such as diethyl ether, tetrahydrofuran, dimethoxyethane and diglyme may preferably be used. In particular, tetrahydrofuran is preferred. The solvent may preferably be used in an amount of from 2 to 50 times by weight, and more preferably from 4 to 10 times by weight, based on the compound of Formula (6).

In the desulfonylation (and deprotection), it is preferable to add a lower alkylamine in the reaction system. This enables improvement in content of polyprenols such as the all trans-form DHP in the reaction product.

As the lower alkylamine, for example, butylamine, diethylamine and diisopropylamine may preferably be used. In particular, diethylamine may preferably be used. The lower alkylamine may preferably be used in a molar equivalent weight of from 1 to 10, and more preferably in a molar equivalent weight of from 2 to 4, based on the compound of Formula (6).

The desulfonylation (and deprotection) may preferably be carried out at a temperature of usually from −50° to 50° C., and more preferably from −30° to 0° C.

Conditions for the desulfonylation (and deprotection) described above are milder and also industrially more advantageous than conventional methods in which alkali metals are reacted in amine type solvents such as ammonia, methylamine and ethylamine at very low temperatures of from −70° to −50° C.

In the case when the protective group is deprotected subsequently after the desulfonylation, it can be deprotected by utilizing any known methods in accordance with protective groups, e.g., by the method described in the publication "Green, Protective Groups in Organic Synthesis, 2nd Edition, John Wiley & Sons (1991)".

After the desulfonylation (and deprotection) is completed, the polyprenols such as DHP can be separated and purified from the reaction mixture by pouring the reaction mixture into water, followed by extraction with a hydrocarbon solvent such as n-hexane or an aromatic solvent such as benzene, and distilling the solvent from the resulting extract by a conventional method.

The polyprenols such as DHP thus isolated may be subjected to a means such as distillation or silica gel column chromatography so as to be more highly purified.

Next, the production process according to the second embodiment of the present invention for producing an allyl halide derivative of (poly)prenol will be described in detail for each step.

Step (A')

In this step, like Step (A) in the first embodiment of the present invention, the secondary allyl alcohol represented by Formula (2) is subjected to five-carbon lengthening reaction n-times (here, n is an integer of 1 or more) which comprises reacting the secondary allyl alcohol represented by the Formula (2) with 2-methyl-3,3-dimethoxy-1-butene and reducing the carbonyl group of the resulting compound, to obtain the compound of Formula (103).

In this step, the protective group for the hydroxyl group, represented by A in Formula (2), may include known protective groups used for the purpose of protecting alcohols, and may include, e.g., an acetyl group, a benzoyl group, a tetrahydropyranyl group, a benzyl group and a t-butyldimethylsilyl group.

The five-carbon lengthening reaction in this step will be described in greater detail with reference to Scheme 11.

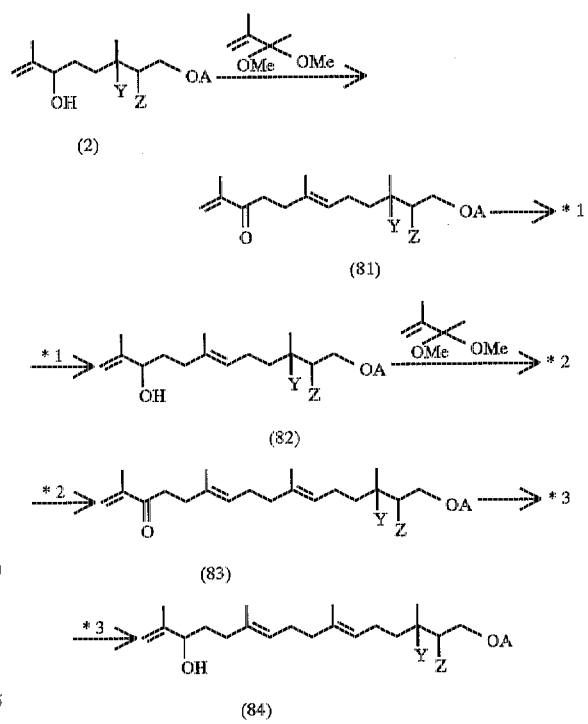

As shown in Scheme 11, in the five-carbon lengthening reaction in this step, the secondary allyl alcohol of Formula (2) is allowed to react with 2-methyl-3,3-dimethoxy-1-butene to obtain a compound of Formula (81). Next, the carbonyl group of the compound of Formula (81) is reduced to convert it to a compound of Formula (82). This compound of Formula (82) corresponds to the compound of Formula (103) in which n is 1.

The compound of Formula (82) is a secondary allyl alcohol, and is subjected to similar five-carbon lengthening reaction, whereby it can be led to a compound of Formula (84) in which the prenyl unit has been extended by one more unit. This compound of Formula (84) corresponds to the compound of Formula (103) in which n is 2.

As in the above, the compounds obtained by successively applying the five-carbon lengthening reaction are all secondary allyl alcohols and, by further five-carbon lengthening reaction, can be converted to compounds in which the prenyl unit has been extended by one more unit.

Thus, the compound represented by Formula (103) can be obtained by subjecting the secondary allyl alcohol of Formula (2) to the five-carbon lengthening reaction n-times.

The 2-methyl-3,3-dimethoxy-1-butene may be used in the five-carbon lengthening reaction may preferably be used in a molar equivalent weight of from 1 to 10, and more preferably in a molar equivalent weight of from 1.1 to 1.5, based on the weight of the compound of Formula (2), Formula (82), Formula (84) or Formula (103) (hereinafter these compounds are each called "substrate").

In the reaction of the substrate with the 2-methyl-3,3-dimethoxy-1-butene, an acid catalyst may preferably be used. As the acid catalyst, a variety of mineral acids or organic acids commonly used may be used, including, e.g., concentrated sulfuric acid, phosphoric acid and p-toluenesulfonic acid. In particular, pyridinium salts of p-toluenesulfonic acid may preferably be used.

The acid catalyst may be used usually in an amount of from 0.01 to 10% by weight, and preferably from 0.05 to 1% by weight, based on the weight of the substrate.

In the reaction of the substrate with the 2-methyl-3,3-dimethoxy-1-butene, it is preferable to use a solvent. As the solvent, aromatic solvents such as benzene, toluene and xylene may preferably be used. In particular, toluene is preferred. The solvent may preferably be used in an amount of from 0.5 to 20 times by weight, and more preferably from 2 to 8 times by weight, based on the weight of the substrate.

In the reaction of the substrate with the 2-methyl-3,3-dimethoxy-1-butene, the reaction may be carried out at a temperature within the range of usually from 50° to 150° C., and preferably from 80° to 110° C., and for a time of usually from 1 to 5 hours.

In the reaction of the substrate with the 2-methyl-3,3-dimethoxy-1-butene, methanol is produced with the progress of reaction. Accordingly, in order to allow the reaction to proceed in a good efficiency, it is preferable to carry out the reaction while distilling outside the system the methanol being produced.

The compounds of Formula (81), Formula (83) and so forth obtained by the reaction of the substrate with the 2-methyl-3,3-dimethoxy-1-butene (hereinafter these compounds are called "$\alpha,\beta$-unsaturated carbonyl compounds") can be reduced by known methods, e.g., a method in which sodium borohydride is reacted in methanol [see Falkner et al, J. Am. Chem. Soc., Vol. 95, p553 (1973)]. The compounds of Formula (82), Formula (84) and Formula (103) can be obtained in high yields by utilizing what is called Meerwein-Ponndorf reduction which uses a secondary alcohol and an aluminum alkoxide.

Here, the Meerwein-Ponndorf reduction may also be carried out after the $\alpha,\beta$-unsaturated carbonyl compound is separated and obtained by a conventional method, from a reaction mixture of the reaction of the substrate with the 2-methyl-3,3-dimethoxy-1-butene. From the viewpoints of the yield of the desired compound and the simplification of operation, the reaction mixture may preferably be subjected to the reduction reaction as it is.

The secondary alcohol used in the Meerwein-Ponndorf reduction may include, e.g., isopropanol and 2-butanol. In particular, isopropanol is preferred.

The secondary alcohol may preferably be used in an amount of 1 to 10 times by weight, and more preferably from 2 to 6 times by weight, based on the weight of the $\alpha,\beta$-unsaturated carbonyl compound.

The aluminum alkoxide used in the Meerwein-Ponndorf reduction may include, e.g., aluminum lower alkoxides such as aluminum ethoxide, aluminum isopropoxide and aluminum 2-butoxide.

The aluminum alkoxide may preferably be used in an amount of from 5 to 100 mol%, and more preferably from 10 to 40 mol%, based on the $\alpha,\beta$-unsaturated carbonyl compound.

The reduction of the $\alpha,\beta$-unsaturated carbonyl compound may be carried out at a temperature within the range of usually from 50° to 150° C., and preferably from 80° to 110° C.

Acetone is produced with the progress of reduction reaction. Accordingly, in order to allow the reaction to proceed in a good efficiency, it is preferable to carry out the reaction while distilling outside the system the acetone being produced.

After the reaction is completed, an acid such as dilute hydrochloric acid or dilute sulfuric acid is added to the reaction mixture in an amount that is in excess with respect to the aluminum alkoxide used in the reaction, to thereby decompose the aluminum alkoxide, and the organic layer obtained is separated. This organic layer is treated by a conventional method to obtain the compound of Formula (103).

The above five-carbon lengthening reaction proceeds stereoselectively and the double bonds newly formed is regulated in the trans form by 95% or more.

The compound of Formula (2), serving as the starting material in this step, can be produced in the manner described with reference to Scheme 10 in FIG. 10.

Step (B')

Like Step (B) in the first embodiment of the present invention, the compound of Formula (103) obtained in Step (A') is halogenized to convert it to the compound of Formula (101). Here, the halogen atom represented by X in Formula (101) may include a chlorine atom and a bromine atom.

It can be halogenized by any conventional methods of converting alcohols to halides. For example, it can be done by allowing a halogenating agent such as thionyl chloride to react with the compound of Formula (103) in a solvent such as isopropyl ether, according to the method described in Japanese Patent Application Laid-open No. 54-76507. The compound of Formula (101) can be thereby obtained in a high yield.

The halogenating agent may preferably be used in a molar equivalent weight of from 0.9 to 2, and more preferably in a molar equivalent weight of from 1 to 1.8, based on the compound of Formula (103). There are no particular limitations on the amount of the solvent used, and the solvent may be used usually in an amount of from 0.5 to 5 times by weight based on the compound of Formula (103).

The halogenation may be carried out at a temperature of usually from −20° to 50° C., and for a time of usually from 0.5 to 24 hours.

After the reaction is completed, the desired compound can be isolated from the reaction mixture by a conventional method. For example, the reaction mixture is poured into aqueous sodium bicarbonate solution, and is subjected to distillation with a solvent including aliphatic hydrocarbon solvents such as n-hexane, aromatic hydrocarbon solvents such as toluene and ether solvents such as diisopropylether, followed by distillation of the solvent from the extract obtained.

Next, the production process according to the third embodiment of the present invention for producing polyprenols in an industrially advantageous manner by utilizing desulfonylation reaction characterized by using an alkali metal and a polycyclic aromatic compound will be described in detail.

In the compounds of Formula (201) and Formula (202), the alkyl group represented by $R^1$ may include, e.g., a methyl group, an ethyl group and a butyl group. The aryl group alternatively represented by $R^1$ may include, e.g., a phenyl group, a tolyl group and a naphthyl group. These alkyl groups or aryl groups may be substituted with a variety of substituents so long as they do not adversely affect the reaction.

The protective group for the hydroxyl group, represented by A in Formula (2), may include known protective groups used for the purpose of protecting alcohols, and may include, e.g., an acetyl group, a benzoyl group, a tetrahydropyranyl group, a benzyl group and a t-butyldimethylsilyl group.

In the compound of Formula (202) used in the present invention, the compound obtain when Y and Z combine to form a carbon-carbon bond is a known compound, and can be produce by, e.g., the method described in Japanese Patent Application Laid-open No. 53-84908. More specifically, as shown by Scheme 6 in FIG. 6, the allyl sulfone compound of Formula (111) is allowed to react with the allyl halide compound of Formula (112) in the presence of a base such as n-butyl lithium.

The allyl sulfone compound of Formula (111) is a known compound as previously stated, and can be obtained by, e.g., brominating a corresponding polyprenyl alcohol with phosphorus tribromide, followed by reaction with a sulfinate such as sodium benzenesulfinate or sodium toluenesulfinate, according to the method described in the publication previously noted, J. Chem. Soc. Perkin Trans. I, p761 (1981). Stated specifically, compounds of Formula (111) in which m is 0, 1, 2 and 3 can be obtained from prenol, geraniol, farnesol and geranyl geraniol, respectively.

The allyl halide compound of Formula (112) can also be produced, as previously described, by protecting the hydroxyl group of a corresponding polyprenol, thereafter selectively epoxidizing the terminal double bond, subjecting the resulting epoxy compound to rearrangement reaction to convert it to a secondary alcohol, and halogenating the alcohol produced, with a halogenating agent such as thionyl chloride or phosphorus tribromide [see Japanese Patent Application Laid-open No. 53-84908 and the publication Terao et al., Synthesis, p467 (1979)]. The route of synthesis is shown by Scheme 12.

SCHEME 12

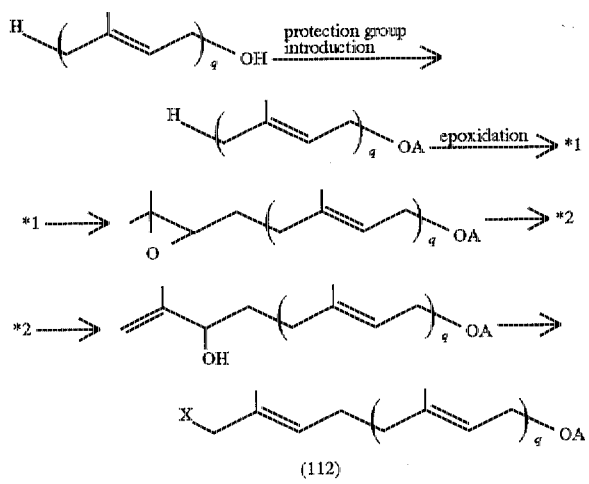

In the compound represented by Formula (202), the compound in which Y and Z are both hydrogen atoms can also be obtained in the same manner as the above. That is, it can be obtained by allowing the allyl sulfone compound of Formula (111) to react with an allyl halide compound of Formula (112') which is derived from a corresponding β,γ-dihydropolyprenol (see Scheme 13). The allyl halide compound of Formula (112') can be obtained also by selectively hydrogenating the double bond at the β- and γ-positions of the allyl halide compound of Formula (112).

SCHEME 13

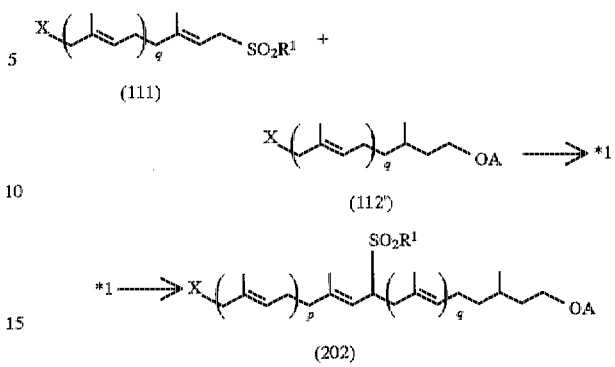

The desulfonylation according to the present invention is carried out by treating the compound represented by Formula (202) (hereinafter often simply called "substrate"), with an alkali metal and a polycyclic aromatic compound.

The alkali metal used in the present invention may include, e.g., lithium, sodium and potassium. The polycyclic aromatic compound used in the present invention may include, e.g., polycyclic aromatic hydrocarbons such as naphthalene, anthracene and biphenyl. From the viewpoint of economical advantage and easiness to handle, it is preferable to use sodium as the alkali metal and naphthalene as the polycyclic aromatic compound.

When the alkali metal and the polycyclic aromatic compound are used, the both may each be added alone in the reaction system, or may be added after, e.g., sodium metal is dispersed in molten naphthalene followed by solidification to form a complex such as a sodium naphthalene complex.

The alkali metal may preferably be used in a molar equivalent weight of from 4 to 20, and more preferably in a molar equivalent weight of from 5 to 10, based on the substrate.

The polycyclic aromatic compound may preferably be used in a molar equivalent weight of from 4 to 20, and more preferably in a molar equivalent weight of from 5 to 10, based on the compound of Formula (6).

The desulfonylation according to the present invention may preferably be carried out in the presence of a solvent. As the solvent, ether type solvents such as diethyl ether, tetrahydrofuran, dimethoxyethane and diglyme may preferably be used. In particular, tetrahydrofuran is preferred.

The solvent may preferably be used in an amount of from 2 to 50 times by weight, and more preferably from 4 to 10 times by weight, based on the substrate.

In the present invention, a lower alkylamine may be added in the reaction system. This enables improvement in content of the compound in which all double bond in the molecule are arranged in the trans form. As the lower alkylamine, for example, butylamine, diethylamine and diisopropylamine may be used. In particular, diethylamine is preferred.

The lower amine may preferably be used in a molar equivalent weight of from 1 to 10, and more preferably in a molar equivalent weight of from 2 to 4, based on the substrate.

The desulfonylation according to the present invention may be carried out at a temperature within the range of usually from −50° to 50° C., and more preferably from −30° to 0° C.

After the reaction is completed, the desired compound can be isolated from the reaction mixture by a conventional method. For example, the reaction mixture is poured into water, and is subjected to distillation with a solvent including aliphatic hydrocarbon solvents such as n-hexane, aromatic hydrocarbon solvents such as toluene and ether solvents such as diisopropylether, followed by distillation of the solvent from the extract obtained.

In the case when the reaction product in which the hydroxyl group has been protected by the protective group A is obtained, the protective group A of the hydroxyl group may be deprotected by utilizing any known methods, e.g., by the method described in the publication "Green, Protective Groups in Organic Synthesis, 2nd Edition, John Wiley & Sons (1991)", so that the product can be led to polyprenols having a free hydroxyl group.

In the desulfonylation according to the present invention, when a benzyl group is used as the protective group A of the hydroxyl group, the protective group A of the hydroxyl group can be deprotected simultaneously at the time of the desulfonylation and hence the polyprenols having a free hydroxyl group can be obtained through one stage.

The polyprenols of Formula (201) obtained by the above process may be subjected to a means such as distillation or silica gel column chromatography so as to be more highly purified.

EXAMPLES

The present invention will be described below in greater detail by giving Examples.

Reference Example A1

(i) Synthesis of farnesyl bromide

Into an argon-replaced 1 liter reaction vessel, 66.6 g (0.3 mol) of farnesol (all trans-form) was charged, and 300 ml of isopropyl ether was further added to dissolve farnesol. The resulting solution was cooled to −20° C., and thereafter 32.5 g (0.12 mol) of phosphorus tribromide was added to carry out reaction at −20° C. to −10° C. for 2 hours. The reaction mixture thus obtained was poured into 400 ml of an aqueous 5% sodium carbonate solution, and the liquid was separated. The organic layer was washed with saturated brine, followed by distillation of the solvent to obtain 77.0 g of farnesyl bromide (yield: 90%). Data of physical properties of this compound are shown below.

FD-mass: $M^+=285$ (ii) Synthesis of farnesyl phenyl sulfone (m=2; $R^1$=phenyl group in Formula (5))

Into an argon-replaced 2 liter reaction vessel, 77.0 g (0.27 mol) of the farnesyl bromide obtained in the above and 59.4 g (0.297 mol) of sodium benzenesulfinate dihydrate were charged, and 250 ml of dimethylformamide was further added to dissolve them to carry out reaction at 20° C. to 30° C. for 3 hours.

Next, to the reaction mixture thus obtained, 500 ml of water was added, followed by extraction with toluene. The extract obtained was washed with saturated brine, followed by distillation of the solvent to obtain 88.7 g of farnesyl phenyl sulfone (yield: 95%). Data of physical properties of this compound are shown below.

FD-mass: $M^+=346$ $^1$H-NMR [300 MHz, $CDCl_3$, δ (ppm)]: 1.30 (s, 3H, $CH_3$), 1.58 (s, 3H, $CH_3$), 1.59 (s, 3H, $CH_3$), 1.67 (s, 3H, $CH_3$), 1.92–2.12 (m, 8H), 3.81 (d, J=8.0 Hz, 2H), 5.02–5.13 (m, 2H), 5.14–5.24 (m, 1H), 7.48–7.90 (m, 5H).

Reference Example A2

(i) Synthesis of prenyl bromide

The procedure of (i) in Reference Example A1 was repeated to obtain prenyl bromide, except that the farnesol was replaced with prenol (0.3 mol). Data of physical properties of this compound are shown below.

FD-mass: $M^+=149$ (ii) Synthesis of prenyl phenyl sulfone (m=4; $R^1$=phenyl group in Formula (5))

The procedure of (ii) in Reference Example A1 was repeated to obtain prenyl phenyl sulfone (yield: 87%), except that the farnesyl bromide was replaced with the total amount of the prenyl bromide obtained in the above reaction. Data of physical properties of this compound are shown below.

FD-mass: $M^+=210$

Reference Example A3

(i) Synthesis of geranyl bromide

The procedure of (i) in Reference Example A1 was repeated to obtain geranyl bromide, except that the farnesol was replaced with geraniol (0.3 mol). Data of physical properties of this compound are shown below.

FD-mass: $M^+=217$ (ii) Synthesis of geranyl phenyl sulfone (m=3; $R^1$=phenyl group in Formula (5))

The procedure of (ii) in Reference Example A1 was repeated to obtain geranyl phenyl sulfone (yield: 85%), except that the farnesyl bromide was replaced with geranyl bromide obtained in the above reaction. Data of physical properties of this compound are shown below.

FD-mass: $M^+=278$

Reference Example A4

(i) Synthesis of geranyl geranyl bromide

The procedure of (i) in Reference Example A1 was repeated to obtain geranyl geranyl bromide, except that the farnesol was replaced with geranyl geraniol (all transform) (0.3 mol). Data of physical properties of this compound are shown below.

FD-mass: $M^+=353$ (ii) Synthesis of geranyl geranyl phenyl sulfone (m=1; $R^1$=phenyl group in Formula (5))

The procedure of (ii) in Reference Example A1 was repeated to obtain geranyl geranyl phenyl sulfone (yield: 82%), except that the farnesyl bromide was replaced with geranyl geranyl bromide obtained in the above reaction. Data of physical properties of this compound are shown below.

FD-mass: $M^+=414$

Example A1

(a) Synthesis of citronellyl benzyl ether (Y,Z =H atoms; A =benzyl group in Formula (71))

Into an argon-replaced reaction vessel, 156 g (1 mol) of citronellol, 139 g (1.1 mols) of benzyl chloride, 240 g of an aqueous 50% sodium hydroxide solution (3 mols in terms of sodium hydroxide) and 3.37 g (0.01 mol) of tetra-n-butylammonium sulfate were successively added at room temperature. Temperature was raised to 50° C., and the mixture was stirred at the same temperature for 3 hours.

After the reaction was completed, the reaction mixture was cooled, followed by addition of toluene to carry out extraction. The toluene layer was washed with water until the aqueous layer became neutral, and thereafter the toluene was distilled. The residue obtained was subjected to vacuum distillation to obtain therefrom 216.2 g of the citronellyl benzyl ether (yield: 87.9%). Data of physical properties of this compound are shown below.

FD-mass: M⁺=246

(b) Synthesis of epoxy compound (Y,Z=H atoms; A=benzyl group in Formula (72))

Into a 2 liter reaction vessel, 196.8 g (0.8 mol) of the citronellyl benzyl ether obtained in the above (a), 123.4 g (0.96 mol) of an aqueous 70% t-butyl hydroperoxide solution and 0.21 g of molybdenyl acetylacetonate(0.1% by weight based on the citronellyl benzyl ether) were charged, and 650 ml of toluene was added to dissolve them. The temperature was raised to 75° C. to 80° C., and the reaction was carried out at the same temperature for 8 hours.

After the reaction was completed, the reaction mixture was cooled to room temperature, followed by addition of 500 ml of an aqueous 5% sodium sulfite solution to decompose excess t-butyl hydroperoxide, and thereafter the liquid was separated. The organic layer obtained was washed with water, and thereafter the solvent was distilled. The residue obtained was subjected to vacuum distillation to obtain 171.9 g of the epoxy compound [Y,Z =H atoms; A=benzyl group in Formula (72)] (yield: 82.0%). Data of physical properties of this compound are shown below.

FD-mass: M⁺=262

(c) Synthesis of allyl alcohol compound (Y,Z=H atoms; A=benzyl group in Formula (2))

Into an argon-replaced 2 liter reaction vessel, 157.2 g (0.6 mol) of the epoxy compound obtained in the above (b) and 42.9 g (0.21 mol) of aluminum isopropoxide were charged, and 850 ml of toluene was added to dissolve them. The temperature of the solution obtained was raised to 100° C. to 110° C., and the reaction was carried out at the same temperature for 8 hours.

After the reaction was completed, the reaction mixture was cooled to room temperature, followed by addition of 300 ml of an aqueous 10% hydrochloric acid solution, and thereafter the liquid was separated. The organic layer was washed with an aqueous 5% sodium carbonate solution and with saturated brine in this order, and then the solvent was distilled. The residue obtained was subjected to vacuum distillation to obtain therefrom 140.7 g of the allyl alcohol compound [Y,Z=H atoms; A=benzyl group in Formula (2)] (yield: 85.0%). Data of physical properties of this compound are shown below.

FD-mass: M⁺=262

$^1$H-NMR [300 MHz, CDCl$_3$, δ (ppm)]: 0.88 (dd, J=1.0, 6.5 Hz, 3H, CH$_3$), 0.98–1.72 (m, 7H), 1.68 (s, 3H, CH$_3$), 2.22 (brs,1H, OH), 3.40–3.54 (m, 2H), 3.95 (t, J=6.4 Hz, 1H), 4.46 (s, 2H), 4.77–4.80 (m, 1H), 4.87–4.90 (brs, 1H), 7.20–7.40 (m, 5H).

(aa) Synthesis of geranyl benzyl ether

Into an argon-replaced reaction vessel, 154 g (1 mol) of geraniol, 139 g (1.1 mols) of benzyl chloride, 240 g (3 mols in terms of sodium hydroxide) of an aqueous 50% sodium hydroxide solution and 3.37 g (0.01 mol) of tetra-n-butylammonium sulfate were successively added at room temperature. Temperature was raised to 50° C., and the mixture was stirred at the same temperature for 3 hours.

After the reaction was completed, the reaction mixture was cooled, followed by addition of 300 ml of toluene to carry out extraction. The toluene layer was washed with water until the aqueous layer became neutral, and thereafter the toluene was distilled. The residue obtained was subjected to vacuum distillation to obtain therefrom 217.2 g of geranyl benzyl ether [Y+Z=carbon----carbon bond; A=benzyl group in Formula (71)] (yield: 89.0%). Data of physical properties of this compound are shown below.

FD-mass: M⁺=244

(bb) Synthesis of epoxy compound

Into a 3 liter reaction vessel, 195.2 g (0.80 mol) of the geranyl benzyl ether obtained in the above (aa), liter of dichloromethane and 1 liter of an aqueous 1.0M sodium hydrogencarbonate solution were charged, followed by little-by-little addition of 161.6 g (0.8 mol; purity: 85%) of m-chloroperbenzoic acid with stirring, and the mixture was further stirred for 2 hours. The reaction mixture obtained was left to stand, and the liquid was separated to form an organic layer. The organic layer obtained was washed with 300 ml of an aqueous 1M sodium hydroxide solution and with 300 ml of water in this order, and thereafter the dichloromethane was distilled. The residue obtained was subjected to vacuum distillation to obtain 191.0 g of the epoxy compound [Y+Z=carbon----carbon bond; A=benzyl group in Formula (72)] (yield: 91.8%). Data of physical properties of this compound are shown below.

FD-mass: M⁺=260

(cc) Synthesis of compound (Y+Z=carbon----carbon bond; A=benzyl group in Formula (2))

Into an argon-replaced 2 liter reaction vessel, 156 g (0.60 mol) of the epoxy compound obtained in the above (bb) and 42.9 g (0.21 mol) of aluminum isopropoxide were charged, and 850 ml of toluene was added to dissolve them. The temperature of the solution obtained was raised to 100° C. to 110° C., and the reaction was carried out at the same temperature for 3 hours.

After the reaction was completed, the reaction mixture was cooled to room temperature, followed by addition of 300 ml of an aqueous 10% hydrochloric acid solution, and thereafter the liquid was separated to form an organic layer. The organic layer was washed with an aqueous 5% sodium carbonate solution and with saturated brine in this order, and then the solvent was distilled. The residue obtained was subjected to vacuum distillation to obtain therefrom 134.1 g of the compound (Y+Z=carbon----carbon bond; A=benzyl group in Formula (2)) (yield: 86.0%). Data of physical properties of this compound are shown below.

FD-mass: M⁺=260

Example A2

(a) Synthesis of allyl alcohol compound (Y,Z=H atoms; m=1; A=benzyl group in Formula (3))

Into a 2 liter reaction vessel, 131.0 g (0.5 mol) of the allyl alcohol compound obtained in (c) of Example A1, 78.0 g (0.6 mol) of 2-methyl-3,3-dimethoxy-1-butene and 0.14 g of pyridinium p-toluenesulfonate were charged, and 50 ml of toluene was added to dissolve them. The solution obtained was heated to 90° C. to 110° C., and the reaction was carried out for 3 hours while distilling outside the reaction system the methanol produced.

The reaction mixture was cooled to room temperature, followed by addition of 20.4 g (0.1 mol) of aluminum isopropoxide and 450 ml of isopropanol, and thereafter again heated to 75° C. to 90° C., where the reaction was carried out for 5 hours while distilling outside the reaction system the acetone produced.

After the reaction was completed, the reaction mixture was cooled to room temperature, followed by addition of 300 ml of an aqueous 5% hydrochloric acid solution, and thereafter the liquid was separated. The organic layer obtained was washed with an aqueous 5% sodium carbonate solution and with saturated brine in this order, and then the solvent was distilled. The residue obtained was subjected to vacuum distillation to obtain therefrom 145.2 g of the allyl alcohol compound (boiling point: 130°–132° C./0.045 torr; yield: 88.0%). Data of physical properties of this compound are shown below.

FD-mass: M$^+$=330

$^1$H-NMR [300 MHz, CDCl$_3$, δ (ppm)]: 0.88 (d, J=6.5 Hz, 3H, CH$_3$), 1.02–1.74 (m, 7H), 1.59 (s, 3H, CH$_3$), 1.69 (s, 3H, CH$_3$), 1.80–2.10 (m, 4H), 2.36 (brs, 1H, OH), 3.40–3.50 (m, 2H), 3.97 (t, J=6.5 Hz, 1H), 4.46 (s, 2H), 4.77–4.80 (m, 1H), 4.90 (brs, 1H), 5.14 (t, J=6.9 Hz, 1H), 7.20–7.35 (m, 5H).

(b) Synthesis of allyl alcohol compound (Y,Z=H atoms; m=2; A=benzyl group in Formula (3))

The procedure of the above (a) was repeated to obtain the allyl alcohol compound (Y,Z=H atoms; m=2; A=benzyl group in Formula (3)) having been five-carbon lengthened (boiling point: 145°–147° C./0.015 torr; yield: 87.0%), except that the allyl alcohol compound [Y,Z=H atoms; A=benzyl group in Formula (2)] was replaced with the allyl alcohol compound [Y,Z=H atoms; m=1; A=benzyl group in Formula (3)] obtained in the above (a). Data of physical properties of this compound are shown below.

FD-mass: M$^+$=398

$^1$H-NMR [300 MHz, CDCl$_3$, δ (ppm)]: 0.88 (d, J=6.5 Hz, 3H, CH$_3$), 1.02–1.74 (m, 7H), 1.59 (s, 6H, 2×CH$_3$), 1.69 (s, 3H, CH$_3$), 1.80–2.10 (m, 8H), 2.36 (brs, 1H, OH), 3.40–3.50 (m, 2H), 3.97 (t, J=6.5 Hz, 1H), 4.47 (s, 2H), 4.78–4.82 (m, 1H), 4.90 (brs, 1H), 5.06–5.17 (m, 2H), 7.20–7.35 (m, 5H).

(c) Synthesis of allyl alcohol compound (Y,Z=H atoms; m=3; A=benzyl group in Formula (3))

The procedure of the above (a) was repeated to obtain the allyl alcohol compound (Y,Z=H atoms; m=3; A=benzyl group in Formula (3)) having been five-carbon lengthened (yield: 83%), except that the allyl alcohol compound [Y,Z=H atoms; A=benzyl group in Formula (2)] was replaced with the allyl alcohol compound (Y,Z=H atoms; m=2; A=benzyl group in Formula (3)) obtained in the above (b). Data of physical properties of this compound are shown below.

FD-mass: M$^+$=466

(d) Synthesis of allyl alcohol compound (Y,Z=H atoms; m=4; A=benzyl group in Formula (3))

The procedure of the above (a) was repeated to obtain the allyl alcohol compound (Y,Z=H atoms; m=4; A=benzyl group in Formula (3)) having been five-carbon lengthened (yield: 79%), except that the allyl alcohol compound [Y,Z=H atoms; A=benzyl group in Formula (2)] was replaced with the allyl alcohol compound [Y,Z=H atoms; m=3; A=benzyl group in Formula (3)] obtained in the above (c). Data of physical properties of this compound are shown below.

FD-mass: M$^+$=534

Example A3

(a) Synthesis of allyl halide compound (Y,Z=H atoms; m=2; X=Cl; A=benzyl group in Formula (4))

Into an argon-replaced 2 liter reaction vessel, 119.4 g (0.3 mol) of the allyl alcohol compound [Y,Z=H atoms; m=2; A=benzyl group in Formula (3)] obtained in (b) of Example A2 and 0.22 g (3 mmols) of dimethylformamide were charged, and 500 ml of isopropyl ether was further added to dissolve them. The resulting solution was cooled to 0° C., and thereafter 57.1 g (0.48 mol) of thionyl chloride was added at the same temperature. Reaction was carried out at 0° C. to 10° C. for 7 hours. Thereafter, the reaction mixture obtained was poured into 1,000 ml of an aqueous 10% sodium carbonate solution, and the liquid was separated. The organic layer was washed with saturated brine, followed by distillation of the solvent to obtain 100 g of the allyl halide compound [Y,Z=H atoms; m=2; X=Cl; A=benzyl group in Formula (4)] (yield: 80%). Data of physical properties of this compound are shown below.

FD-mass: M$^+$=416.5

$^1$H-NMR [300 MHz, CDCl$_3$, δ (ppm)]: 0.89 (d, J=6.5 Hz, 3H, CH$_3$), 1.06–1.80 (m, 5H), 1.59 (s, 6H, 2×CH$_3$), 1.71 (s, 3H, CH$_3$), 1.88–2.18 (m, 10H), 3.42–3.58 (m, 2H), 3.97 (s, 2H), 4.48 (s, 2H), 5.11 (t, J=6.6 Hz, 2H), 5.48 (t, J=6.7 Hz, 1H), 7.20–7.35 (m, 5H).

(b) Synthesis of allyl halide compound (Y,Z=H atoms; m=1; X=Cl; A=benzyl group in Formula (4))

The procedure of the above (a) was repeated to obtain the allyl halide compound [Y,Z=H atoms; m=1; X=Cl; A=benzyl group in Formula (4)] (yield: 82%), except that the allyl alcohol compound [Y,Z=H atoms; m=2; A=benzyl group in Formula (3)] was replaced with the allyl alcohol compound [Y,Z=H atoms; m=1; A=benzyl group in Formula (3)] obtained in (a) of Example A2. Data of physical properties of this compound are shown below.

FD-mass: M$^+$=348.5

(c) Synthesis of allyl halide compound (Y,Z=H atoms; m=3; X=Cl; A=benzyl group in Formula (4))

The procedure of the above (a) was repeated to obtain the allyl halide compound [Y,Z=H atoms; m=3; X=Cl; A=benzyl group in Formula (4)] (yield: 78%), except that the allyl alcohol compound [Y,Z=H atoms; m=2; A=benzyl group in Formula (3)] was replaced with the allyl alcohol compound [Y,Z=H atoms; m=3; A=benzyl group in Formula (3)] obtained in (c) of Example A2. Data of physical properties of this compound are shown below.

FD-mass: M$^+$=484.5

(d) Synthesis of allyl halide compound (Y,Z=H atoms; m=4; X=Cl; A=benzyl group in Formula (4))

The procedure of the above (a) was repeated to obtain the allyl halide compound [Y,Z=H atoms; m=4; X=Cl; A=benzyl group in Formula (4)] (yield: 75%), except that the allyl alcohol compound [Y,Z=H atoms; m=2; A=benzyl group in Formula (3)] was replaced with the allyl alcohol compound [Y,Z=H atoms; m=4; A=benzyl group in Formula (3)] obtained in (d) of Example A2. Data of physical properties of this compound are shown below.

FD-mass: M$^+$=552.5

Example A4

(a) Synthesis of Formula-(6) condensate (Y,Z=H atoms; m=2; A=benzyl group)

Into an argon-replaced 1 liter reaction vessel, 83.3 g (0.2 mol) of the allyl halide compound of Formula (4) (Y,Z=H atoms; m=2; X=Cl) obtained in (a) of Example A3 and 69.2 g (0.2 mol) of the farnesyl phenyl sulfone of Formula (5) (m=2) obtained in Reference Example A1 were charged, and 300 ml of N-methylpyrrolidone was added to dissolve them. The resulting solution was cooled to 0° C., and subsequently 38.4 g (0.4 mol) of sodium t-butoxide was added. Internal temperature was raised to room temperature, and the reaction was further carried out at the same temperature for 2 hours.

The reaction mixture obtained was poured into 1,000 ml of ice-cooled water, and was subjected to extraction with toluene. The extract obtained was washed with saturated brine, followed by distillation of the solvent to obtain 130.9 g of the condensate of Formula (6) (Y,Z=H atoms; m=2) (yield: 90%). Data of physical properties of this compound are shown below.

FD-mass: M$^+$=726

$^1$H-NMR [300 MHz, CDCl$_3$, δ (ppm)]: 0.88 (d, J=6.5 Hz, CH$_3$), 1.10–1.80 (m, 5H), 1.15 (s, 3H, CH$_3$), 1.52 (s, 3H, CH$_3$), 1.55 (s, 3H, CH$_3$), 1.58 (s, 3H, CH$_3$), 1.59 (s, 6H, 2×CH$_3$), 1.67 (s, 3H, CH$_3$), 1.86–2.12 (m, 18H), 2.29 (dd, J=11.6, 12.8 Hz, 1H), 2.88 (d, J=13.1 Hz, 1H), 3.43–3.55 (m, 2H), 3.88 (ddd, J=10.8, 10.8, 3.0 Hz, 1H), 4.48 (s, 2H), 4.91 (d, J=10.8 Hz, 1H), 5.00–5.18 (m, 5H), 7.20–7.35 (m, 5H), 7.42–7.62 (m, 3H), 7.80–7.86 (m, 2H).

(b) Synthesis of Formula-(6) condensate (Y,Z=H atoms; m=1; A=benzyl group)

The procedure of the above (a) was repeated to obtain the condensate of Formula (6) (Y,Z=H atoms; m=1) (yield: 91%), except that the allyl halide compound of Formula (4) (Y,Z=H atoms; m=2; X=Cl) was replaced with the allyl halide compound of Formula (4) (Y,Z=H atoms; m=1; X=Cl) obtained in (b) of Example A3 and also the farnesyl phenyl sulfone of Formula (5) (m=2) was replaced with the geranyl geranyl phenyl sulfone of Formula (5) (m=1) obtained in Reference Example A4. Data of physical properties of this compound are shown below.

FD-mass: $M^+$=726

(c) Synthesis of Formula-(6) condensate (Y,Z=H atoms; m=3; A=benzyl group)

The procedure of the above (a) was repeated to obtain the condensate of Formula (6) (Y,Z=H atoms; m=3) (yield: 88%), except that the allyl halide compound of Formula (4) (Y,Z=H atoms; m=2; X=Cl) was replaced with the allyl halide compound of Formula (4) (Y,Z=H atoms; m=3; X=Cl) obtained in (c) of Example A3 and also the farnesyl phenyl sulfone of Formula (5) (m=2) was replaced with the geranyl phenyl sulfone of Formula (5) (m=3) obtained in Reference Example A3.

(d) Synthesis of Formula-(6) condensate (Y,Z=H atoms; m=4; A=benzyl group)

The procedure of the above (a) was repeated to obtain the condensate of Formula (6) (Y,Z=H atoms; m=4) (yield: 88%), except that the allyl halide compound of Formula (4) (Y,Z=H atoms; m=2; X=Cl) was replaced with the allyl halide compound of Formula (4) (Y,Z=H atoms; m=4; X=Cl) obtained in (d) of Example A3 and also the farnesyl phenyl sulfone of Formula (5) (m=2) was replaced with the prenyl phenyl sulfone of Formula (5) (m=4) obtained in Reference Example A2. Data of physical properties of this compound are shown below.

FD-mass: $M^+$=726

Example A5

(a) Synthesis of DHP

Into an argon-replaced 2 liter reaction vessel, 72.7 g (0.1 mol) of the condensate of Formula (6) (Y,Z=H atoms; m=2; A=benzyl group) obtained in (a) of Example A4 and 14.6 g (0.2 mol) of diethylamine were charged, and 600 ml of tetrahyrofuran was added to dissolve them, followed by cooling to −30° C. t−20° C. To the solution obtained, 77.0 g (0.6 mol in terms of sodium) of a sodium-naphthalene complex (sodium content: about 18% by weight) was added at the same temperature, and the reaction was further carried out at −10° C. to 0° C. for 2 hours.

Next, the reaction mixture obtained was poured into 1,000 ml of a saturated aqueous ammonium chloride solution, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 31.8 g of DHP (yield: 64%). Data of physical properties of the DHP obtained are shown below.

FD-mass: $M^+$=496

$^1$H-NMR [300 MHz, CDCl$_3$, δ (ppm)]: 0.90 (d, J=6.6 Hz, 3H, CH$_3$), 1.10–1.70 (m, 5H), 1.59 (s, 18H, 6×CH$_3$), 1.67 (s, 3H, CH$_3$), 1.90–2.14 (m, 22H), 3.57–3.72 (m, 2H), 5.05–5.16 (m, 6H)

(b) Synthesis of DHP

The procedure of the above (a) was repeated to obtain DHP (yield: 70%), except that the condensate of Formula (6) (Y,Z=H atoms; m=2; A=benzyl group) was replaced with the condensate of Formula (6) (Y,Z=H atoms; m=1; A=benzyl group) obtained in (b) of Example A4. Data of physical properties of this DHP were the same as those obtained in the above (a).

(c) Synthesis of DHP

The procedure of the above (a) was repeated to obtain DHP (yield: 65%), except that the condensate of Formula (6) (Y,Z=H atoms; m=2; A=benzyl group) was replaced with the condensate of Formula (6) (Y,Z=H atoms; m=3; A=benzyl group) obtained in (c) of Example A4. Data of physical properties of this DHP were the same as those obtained in the above (a).

(d) Synthesis of DHP

The procedure of the above (a) was repeated to obtain DHP (yield: 67%), except that the condensate of Formula (6) (Y,Z=H atoms; m=2; A=benzyl group) was replaced with the condensate of Formula (6) (Y,Z=H atoms; m=4; A=benzyl group) obtained in (d) of Example A4. Data of physical properties of this DHP were the same as those obtained in the above (a).

Example A6

The procedure of (a) in Example A5 was repeated to carry out the reaction and treatment to obtain 30.8 g of DHP (yield: 62%), except that the compound of Formula (6) in which A is a benzyl group was replaced with the compound of Formula (6) in which A is an acetyl group.

Example A7

The procedure of (a) in Example A5 was repeated to carry out the reaction, except that the compound of Formula (6) in which A is a benzyl group was replaced with the compound of Formula (6) in which A is a tetrahydropyranyl group.

The reaction mixture obtained was poured into 1,000 ml of a saturated aqueous ammonium chloride solution, and was subjected to extraction with n-hexane. The extract obtained was washed with saturated brine, and then the solvent was distilled. To the residue obtained, 500 ml of methanol and 1 g of p-toluenesulfonic acid were added, and the reaction was carried out for 5 hours.

Next, the reaction mixture obtained was poured into 100 ml of an aqueous sodium hydrogencarbonate solution, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 33.7 g of DHP (yield: 68%).

Example A8

The procedure of (a) in Example A5 was repeated to carry out the reaction, except that the compound of Formula (6) in which A is a benzyl group was replaced with the compound of Formula (6) in which A is a t-butyldimethylsilyl group.

The reaction mixture obtained was poured into 1,000 ml of a saturated aqueous ammonium chloride solution, and was subjected to extraction with n-hexane. The extract obtained was washed with saturated brine, and then the solvent was distilled. To the residue obtained, 500 ml of tetrahydrofuran and 100 ml of a tetrahydrofuran solution (1M) of tetrabutylammonium fluoride were added, and the reaction was carried out at room temperature for 1 hour.

Next, the reaction mixture obtained was poured into 1,000 ml of water, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 32.7 g of DHP (yield: 66%).

Example B1

Synthesis of Formula-(103) compound (Y+Z=carbon—carbon bond; n=1; A=benzyl group)

Into a 2 liter reaction vessel, 130 g (0.5 mol) of the compound of Formula (2) (Y+Z=carbon-carbon bond; A=benzyl group) obtained in (cc) of Example A1, 78.0 g (0.6 mol) of 2-methyl-3,3-dimethoxy-1-butene and 0.14 g of pyridinium p-toluenesulfonate were charged, and 450 ml of toluene was added to dissolve them. The solution obtained was heated to 90° C. to 110° C., and the reaction was carried out for 3 hours while distilling outside the reaction system the methanol produced.

The reaction mixture was cooled to room temperature, followed by addition of 20.4 g (0.1 mol) of aluminum isopropoxide and 450 ml of isopropanol, and thereafter again heated to 75° C. to 90° C., where the reaction was carried out for 5 hours while distilling outside the reaction system the acetone produced.

After the reaction was completed, the reaction mixture was cooled to room temperature, followed by addition of 300 ml of an aqueous 5% hydrochloric acid solution to effect hydrolysis, and then the liquid was separated to form an organic layer. The organic layer was washed with an aqueous 5% sodium carbonate solution and with saturated brine in this order, and thereafter the solvent was distilled to obtain 141.0 g of the compound of Formula (103) (Y+Z=carbon-carbon bond; n=1; A=benzyl group) (yield: 86%). Data of physical properties of this compound are shown below.

FD-mass: $M^+=328$

Example B2

Synthesis of Formula-(103) compound (Y+Z=carbon—carbon bond; n=2; A=benzyl group)

Into a 2 liter reaction vessel, 131 g (0.4 mol) of the compound of Formula (103) (Y+Z=carbon-carbon bond; n=1; A=benzyl group) obtained in Example B1, 62.4 g (0.48 mol) of 2-methyl-3,3-dimethoxy-1-butene and 0.14 g of pyridinium p-toluenesulfonate were charged, and 450 ml of toluene was added to dissolve them. The solution obtained was heated to 90° C. to 110° C., and the reaction was carried out for 3 hours while distilling outside the reaction system the methanol produced.

The reaction mixture was cooled to room temperature, followed by addition of 16.3 g (0.08 mol) of aluminum isopropoxide and 450 ml of isopropanol, and thereafter again heated to 75° C. to 90° C., where the reaction was carried out for 5 hours while distilling outside the reaction system the acetone produced.

After the reaction was completed, the reaction mixture was cooled to room temperature, followed by addition of 250 ml of an aqueous 5% hydrochloric acid solution to effect hydrolysis, and then the liquid was separated to form an organic layer. The organic layer was washed with an aqueous 5% sodium carbonate solution and with saturated brine in this order, and thereafter the solvent was distilled to obtain 135 g of the compound of Formula (103) (Y+Z=carbon—carbon bond; n=2; A=benzyl group) (yield: 85%). Data of physical properties of this compound are shown below.

FD-mass: $M^+=396$

Example B3

Synthesis of Formula-(103) compound (Y+Z=carbon—carbon bond; n=3; A=benzyl group)

The procedure of Example B1 was repeated to obtain 112.8 g of the compound of Formula (103) (Y+Z=carbon—carbon bond; n=3; A=benzyl group) (yield: 81%), except that the compound of Formula (2) [Y+Z=carbon—carbon bond; A=benzyl group] was replaced with 111.8 g (0.3 mol) of the compound of Formula (103) (Y+Z=carbon—carbon bond; n=2; A=benzyl group) obtained in Example B2 was used. Data of physical properties of this compound are shown below.

FD-mass: $M^+=464$

Example B4

Synthesis of Formula-(103) compound (Y+Z=carbon—carbon bond; n=4; A=benzyl group)

The procedure of Example B1 was repeated to obtain 129.3 g of the compound of Formula (103) (Y+Z=carbon—carbon bond; n=4; A=benzyl group) (yield: 81%), except that the compound of Formula (2) [Y+Z=carbon—carbon bond; A=benzyl group] was replaced with 139.2 g (0.3 mol) of the compound of Formula (103) (Y+Z=carbon—carbon bond; n=3; A=benzyl group) obtained in Example B3 was used. Data of physical properties of this compound are shown below.

FD-mass: $M^+=532$

Example B5

Synthesis of Formula-(103) compound (Y,Z=H atoms; n=1; A=benzyl group)

The procedure of Example B1 was repeated to obtain 45 g of the compound of Formula (103) (Y,Z=H atoms; n=1; A=benzyl group) (yield: 88%), except that the compound of Formula (2) [Y+Z=carbon—carbon bond; A=benzyl group] was replaced with 131 g (0.5 mol) of the compound of Formula (2) (Y,Z=H atoms; A=benzyl group) obtained in (c) of Example A1 was used. Data of physical properties of this compound are shown below.

FD-mass: $M^+=330$ $^1$H-NMR [300 MHz, CDCl$_3$, δ (ppm)]: 0.88 (d, J=6.5 Hz, 3H, CH$_3$), 1.02–1.74 (m, 7H), 1.59 (s, 3H, CH$_3$), 1.69 (s, 3H, CH$_3$), 1.80–2.10 (m, 4H), 2.36 (brs, 1H, OH), 3.40–3.50 (m, 2H), 3.97 (t, J=6.5 Hz, 1H), 4.46 (s, 2H), 4.77–4.80 (m, 1H), 4.90 (brs, 1H), 5.14 (t, J=6.9 Hz, 1H), 7.20–7.35 (m, 5H).

Example B6

Synthesis of Formula-(103) compound (Y,Z=H atoms; n=2; A=benzyl group)

The procedure of Example B1 was repeated to obtain 139 g of the compound of Formula (103) (Y,Z=H atoms; n=2; A=benzyl group) (yield: 87%), except that the compound of Formula (2) [Y+Z=carbon—carbon bond; A=benzyl group] was replaced with 132 g (0.4 mol) of the compound of Formula (103) (Y,Z=H atoms; n=1; A=benzyl group) obtained in Example B5 was used. Data of physical properties of this compound are shown below.

FD-mass: $M^+398$ $^1$H-NMR [300 MHz, CDCl$_3$, δ(ppm)]: 0.88 (d, J=6.5 Hz, 3H, CH$_3$), 1.02–1.74 (m, 7H), 1.59 (s, 6H, 2×CH$_3$), 1.69 (s, 3H, CH$_3$), 1.80–2.10 (m, 8H), 2.36 (brs, OH), 3.40–3.50 (m, 2H), 3.97 (t, J=6.5 Hz, 1H), 4.47 (s, 2H), 4.78–4.82 (m, 1H), 4.90 (brs, 1H), 5.06–5.17 (m, 2H), 7.20–7.35 (m, 5H).

Example B7

Synthesis of Formula-(103) compound (Y,Z=H atoms; n=3; A=benzyl group)

The procedure of Example B1 was repeated to obtain 117.4 g of the compound of Formula (103) (Y,Z=H atoms; n=3; A=benzyl group) (yield: 83%), except that the compound of Formula (2) [Y+Z=carbon—carbon bond; A=benzyl group] was replaced with 119.4 g (0.3 mol) of the compound of Formula (103) (Y,Z=H atoms; n=2; A=benzyl group) obtained in Example B6 was used. Data of physical properties of this compound are shown below.

FD-mass: $M^+=466$

Example B8

Synthesis of Formula-(103) compound (Y,Z=H atoms; n=4; A=benzyl group)

The procedure of Example B1 was repeated to obtain 126.6 g of the compound of Formula (103) (Y,Z=H atoms; n=4; A=benzyl group) (yield: 79%), except that the compound of Formula (2) [Y+Z=carbon—carbon bond; A=benzyl group] was replaced with 139.8 g (0.3 mol) of the compound of Formula (103) (Y,Z=H atoms; n=3; A=benzyl group) obtained in Example B7 was used. Data of physical properties of this compound are shown below.

FD-mass: $M^+=534$

Example B9

Synthesis of Formula-(103) compound (Y+Z=carbon—carbon bond; n=1; A=t-butyldimethylsilyl group)

The procedure of Example B1 was repeated to obtain 133.6 g of the compound of Formula (103) (Y+Z=carbon—carbon bond; n=1; A=t-butyldimethylsilyl group) (yield: 83%), except that the compound of Formula (2) [Y+Z=carbon—carbon bond; A=benzyl group] was replaced with 127 g (0.5 mol) of the compound of Formula (2) (Y+Z=carbon—carbon bond; A=t-butyldimethylsilyl group) was used. Data of physical properties of this compound are shown below.

FD-mass: $M^+=352$

Example B10

Synthesis of Formula-(103) compound (Y+Z=carbon—carbon bond; n=1; A=benzoyl group)

The procedure of Example B1 was repeated to obtain 123.8 g of the compound of Formula (103) (Y+Z=carbon—carbon bond; n=1; A=benzoyl group) (yield: 75%), except that the compound of Formula (2) [Y+Z=carbon—carbon bond; A=benzyl group] was replaced with 131 g (0.5 mol) of the compound of Formula (2) (Y+Z=carbon—carbon bond; A=benzoyl group) was used. Data of physical properties of this compound are shown below.

FD-mass: $M^+=342$

Example B11

Synthesis of Formula-(103) compound (Y,Z=H atoms; n=1; A=t-butyldimethylsilyl group)

The procedure of Example B1 was repeated to obtain 137.7 of the compound of Formula (103) (Y,Z=H atoms; n=1; A=t-butyldimethylsilyl group) (yield: 85%), except that the compound of Formula (2) [Y+Z=carbon—carbon bond; A=benzyl group] was replaced with 128 g (0.5 mol) of the compound of Formula (2) (Y,Z=H atoms; A=t-butyldimethylsilyl group) was used. Data of physical properties of this compound are shown below.

FD-mass: $M^+=354$

Example B12

Synthesis of Formula-(103) compound (Y,Z=H atoms; n=1; A=benzoyl group)

The procedure of Example B1 was repeated to obtain 126.2 of the compound of Formula (103) (Y,Z=H atoms; n=1; A=benzoyl group) (yield: 76%), except that the compound of Formula (2) [Y+Z=carbon—carbon bond; A=benzyl group] was replaced with 132 g (0.5 mol) of the compound of Formula (2) (Y,Z=H atoms; A=benzoyl group) was used. Data of physical properties of this compound are shown below.

FD-mass: $M^+=344$

Example B13

Synthesis of Formula-(101) compound (Y,Z=H atoms; X=Cl; n=2; A=benzyl group)

Into an argon-replaced 2 liter reaction vessel, 119.4 g (0.3 mol) of the compound of Formula (103) (Y,Z=H atoms; n=2; A=benzyl group) obtained in Example B6 and 0.22 g (3 mmols) of dimethylformamide were charged, and 500 ml of isopropyl ether was added to dissolve them. The resulting solution was cooled to 0° C., and thereafter 57.1 g (0.48 mol) of thionyl chloride was added at the same temperature. Reaction was carried out at 0° C. to 10° C. for 7 hours. The reaction mixture obtained was poured into 1 liter of an aqueous 10% sodium carbonate solution, and the liquid was separated to form an organic layer. The organic layer obtained was washed with saturated brine, followed by distillation of the solvent to obtain 100 g of the compound of Formula (101) (Y,Z=H atoms; X=Cl; n=2; A=benzyl group) (yield: 80%). Data of physical properties of this compound are shown below.

FD-mass: $M^+=416.5$

Examples B14 to B20

The procedure of Example B13 was repeated to obtain corresponding compounds of Formula (101), except that the compound of Formula (103) (Y,Z=H atoms; n=2; A=benzyl group) was replaced with 0.3 mol of the compounds of Formula (103) obtained in Examples B5, B7, B8 and Examples B1 to B4, respectively, were used. Yield and data of physical properties of these are shown in Table 1. In Table 1, Bn represents a benzyl group.

TABLE 1

| Example | Compound of Formula (103) | Compound of Formula (101) | Yield (%) | FD-mass (M+) |
|---|---|---|---|---|
| B14 | 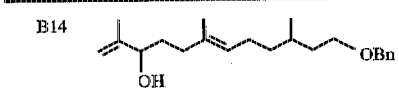 | | 82 | 348.5 |

TABLE 1-continued

| Example | Compound of Formula (103) | Compound of Formula (101) | Yield (%) | FD-mass (M⁺) |
|---|---|---|---|---|
| B15 | (structure, n=3, OH, OBn) | (structure, Cl, n=3, OBn) | 78 | 484.5 |
| B16 | (structure, n=4, OH, OBn) | (structure, Cl, n=4, OBn) | 75 | 552.5 |
| B17 | (structure, OH, OBn) | (structure, Cl, OBn) | 81 | 346.5 |
| B18 | (structure, n=2, OH, OBn) | (structure, Cl, n=2, OBn) | 77 | 414.5 |
| B19 | (structure, n=3, OH, OBn) | (structure, Cl, n=3, OBn) | 76 | 482.5 |
| B20 | (structure, n=4, OH, OBn) | (structure, Cl, n=4, OBn) | 74 | 550.5 |

Reference Example C1

Synthesis of Formula-(202) compound (Y+Z=carbon—carbon bond; p=2; q=1; A=benzyl group)

Into an argon-replaced 1 liter reaction vessel, 55.7 g (0.2 mol) of the allyl halide compound of Formula (112) (q=1, X=Cl; A=benzyl group) and 69.2 g (0.2 mol) of the allyl sulfone compound (farnesyl phenyl sulfone) of Formula (111) in which p is 2 were charged, and 300 ml of N-methylpyrrolidone was added to dissolve them. The resulting solution was cooled to 0° C., and then 38.4 g (0.4 mol) of sodium t-butyrate was added. Internal temperature was raised to room temperature, and the reaction was further carried out at the same temperature for two hours.

The reaction mixture obtained was poured into 1 liter of ice-cooled water, and was subjected to extraction with toluene. The extract obtained was washed with saturated brine, followed by distillation of the solvent to obtain 101.1 g of the compound of Formula (202) (Y+Z=carbon—carbon bond; p=2; q=1; A=benzyl group) (yield: 86%).

Data of physical properties of the compound obtained are shown below.

FD-mass: M⁺=588

Reference Example C2

Synthesis of Formula-(202) compound (Y,Z=H atoms; p=2; q=1; A=benzyl group)

Into an argon-replaced 1 liter reaction vessel, 56.1 g (0.2 mol) of the allyl halide compound of Formula (112') (Y,Z=H atoms; q=1, X=Cl; A=benzyl group) and 69.2 g (0.2 mol) of the allyl sulfone compound (farnesyl phenyl sulfone) of Formula (111) in which p is 2 were charged, and 300 ml of N-methylpyrrolidone was added to dissolve them. The resulting solution was cooled to 0° C., and then 38.4 g (0.4 mol) of sodium t-butoxide was added. Internal temperature was raised to room temperature, and the reaction was further carried out at the same temperature for two hours.

The reaction mixture obtained was poured into 1 liter of ice-cooled water, and was subjected to extraction with toluene. The extract obtained was washed with saturated brine, followed by distillation of the solvent to obtain 107.4 g of the compound of Formula (202) (Y,Z=H atoms; p=2; q=1; A=benzyl group) (yield: 91%).

Data of physical properties of the compound obtained are shown below.

FD-mass: M⁺=590

Reference Examples C3 to C5

The procedure of Reference Example C1 was repeated to obtain corresponding compounds of Formula (202), except that the allyl halide compound of Formula (112) (q=1; X=Cl; A=benzyl group) was replaced with ally halide compounds of Formula (112) and allyl sulfone compounds of Formula (111) as shown in Table 2 were respectively used. The ally halide compounds of Formula (112) and allyl sulfone compounds of Formula (111) were each used in an amount of 0.2 mol. Yield and data of physical properties (FD-mass) of these are shown together in Table 2. In Table 2, Bn represents a benzyl group.

TABLE 2

| Reference Example | Allyl halide compound of Formula (112) | Allyl sulfone compound of Formula (111) | Compound of Formula (202) | Yield (%) | FD-mass (M⁺) |
|---|---|---|---|---|---|
| C3 | X = Cl, A = Bn, q = 0<br>Y, Z: C—C bond | p = 2, R¹ = Ph | | 92 | 520 |
| C4 | X = Cl, A = Bn, q = 3<br>Y, Z: C—C bond | p = 1, R¹ = Ph | | 85 | 656 |
| C5 | X = Cl, A = Bn, q = 3<br>Y, Z: C—C bond | p = 3, R¹ = Ph | | 83 | 792 |

Reference Examples C6 to C8

The procedure of Reference Example C2 was repeated to obtain corresponding compounds of Formula (202), except that the allyl halide compound of Formula (112')(Y,Z=H atoms; q=1; X=Cl; A=benzyl group) was replaced with ally halide compounds of Formula (112') and allyl sulfone compounds of Formula (111) as shown in Table 3 were respectively used. The ally halide compounds of Formula (112') and allyl sulfone compounds of Formula (111) were each used in an amount of 0.2 mol. Yield and data of physical properties (FD-mass) of these are shown together in Table 3. In Table 3, Bn represents a benzyl group.

the reaction mixture obtained, 77 g (0.6 mol in terms of sodium) of a sodium-naphthalene complex (sodium content: about 18% by weight) was added at the same temperature, and the reaction was further carried out at −10° C. to 0° C. for 2 hours.

The reaction mixture obtained was poured into 1 liter of a saturated aqueous ammonium chloride solution, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 22.2 g of 3,7,11,15,19-pentamethyl-2,6-10,14,18-

TABLE 3

| Reference Example | Allyl halide compound of Formula (112') | Allyl sulfone compound of Formula (111) | Compound of Formula (202) | Yield (%) | FD-mass (M⁺) |
|---|---|---|---|---|---|
| C6 | X = Cl, A = Bn, q = 1<br>Y = Z = H | p = 1, R¹ = Ph | | 89 | 522 |
| C7 | X = Cl, A = Bn, q = 2<br>Y = Z = H | p = 0, R¹ = Ph | | 90 | 522 |
| C8 | X = Cl, A = Bn, q = 3<br>Y = Z = H | p = 3, R¹ = Ph | | 81 | 794 |

Example C1

Synthesis of Formula-(201) compound (Y+Z=carbon—carbon bond; p=2; q=1; R² =H)

Into an argon-replaced 2 liter reaction vessel, 58.8 g (0.1 mol) of the compound of Formula (202) (Y+Z=carbon—carbon bond; p=2; q=1; A=benzyl group) obtained in Reference Example C1 and 14.6 g (0.2 mol) of diethylamine were charged, and 600 ml of tetrahydrofuran was added to dissolve them, followed by cooling to −30° C. t −20° C. To eicosapentaen-1-ol (the compound of Formula (201); Y+Z=carbon—carbon bond; p=2; q=1; R² =H) (yield: 62%).

Data of physical properties of the DHP obtained are shown below.

FD-mass: M⁺=358

Example C2

Synthesis of Formula-(201) compound (Y,Z=H atoms; p=2; q=1; R² =H)

Into an argon-replaced 2 liter reaction vessel, 59.0 g (0.1 mol) of the compound of Formula (202) (Y,Z=H atoms; p=2; q=1; A=benzyl group) obtained in Reference Example C2 and 14.6 g (0.2 mol) of diethylamine were charged, and 600 ml of tetrahyrofuran was added to dissolve them, followed by cooling to −30° C. t −20° C. To the reaction mixture obtained, 77 g (0.6 mol in terms of sodium) of a sodium-naphthalene complex (sodium content: about 18% by weight) was added at the same temperature, and the reaction was further carried out at −10° C. to 0° C. for 2 hours.

The reaction mixture obtained was poured into 1 liter of a saturated aqueous ammonium chloride solution, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 24.8 g of 3,7,11,15,19-pentamethyl-2,6-10,14-eicosatetraen-1-ol (the compound of Formula (1); Y,Z=H atoms; p=2; q=1; $R^2$=H) (yield: 69%).

Data of physical properties of the DHP obtained are shown below.

FD-mass: $M^+$=360

Examples C3 to C8

The procedure of Example C1 was repeated to obtain corresponding compounds of Formula (201), except that the compound of Formula (202) (Y+Z=carbon—carbon bond; p=2; q=1; A=benzyl group) was replaced with 0.1 mol of the compounds obtained in Reference Examples C3 to C8, respectively, as the compound of Formula (202) were used.

Yield and data of physical properties of these are shown in Table 4. In Table 4, Bn represents a benzyl group.

TABLE 4

| Example | Compound of Formula (202) | Compound of Formula (201) | Yield (%) | FD-mass ($M^+$) |
|---|---|---|---|---|
| C3 | | | 63 | 290 |
| C4 | | | 59 | 426 |
| C5 | | | 58 | 562 |
| C6 | | | 72 | 292 |
| C7 | | | 71 | 292 |
| C8 | | | 66 | 564 |

Example C9

Synthesis of Formula-(201) compound (Y,Z=H atoms; p=2; q=1; $R^2$=H)

The procedure of Example C2 was repeated to obtain 25.6 g of 3,7,11,15,19-pentamethyl-2,6-10,14-eicosatetraen-1-ol (the compound of Formula (201); Y,Z=H atoms; p=2; q=1; =H) (yield: 71%), except that the compound of Formula (202) (Y,Z=H atoms; p=2; q=1; A: benzyl group) was replaced with 55.4 g (0.1 mol) of the compound of Formula (202) (Y,Z=H atoms; p=2; q=1; A: acetyl group) was used.

Example C10

Synthesis of Formula-(201) compound (Y,Z=H atoms; p=2; q=1; $R^2$=H)

Into an argon-replaced 2 liter reaction vessel, 50.8 g (0.1 mol) of the compound of Formula (202) (Y,Z=H atoms; p=2; q=1; A=tetrahydropyranyl group) and 14.6 g (0.2 mol) of diethylamine were charged, and 600 ml of tetrahyrofuran was added to dissolve them, followed by cooling to −30° C. t −20° C. To the reaction mixture obtained, 77 g (0.6 mol in terms of sodium) of a sodium-naphthalene complex (sodium content: about 18% by weight) was added at the same temperature, and the reaction was further carried out at −10° C. to 0° C. for 2 hours. The reaction mixture obtained was poured into 1 liter of a saturated aqueous ammonium chloride solution, and was subjected to extraction with n-hexane. The extract obtained was washed with saturated brine, and then the solvent was distilled.

To the residue obtained, 500 ml of methanol and 1 g of p-toluenesulfonic acid were added, and the reaction was carried out at room temperature for 5 hours. The reaction mixture obtained was poured into 1 liter of an aqueous sodium haydrogencarbonate solution, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 25.2 g of 3,7,11,15,19-pentamethyl-2,6-10,14-eicosatetraen-1-ol (the compound of Formula (201); Y,Z=H atoms; p=2; q=1; $R^2$=H) (yield: 70%).

Example C11

Synthesis of Formula-(201) compound (Y,Z=H atoms; p=2; q=1; $R^2$=H)

Into an argon-replaced 2 liter reaction vessel, 62.6 g (0.1 mol) of the compound of Formula (202) (Y,Z=H atoms; p=2; q=1; A=t-butyldimethylsilyl group) and 14.6 g (0.2 mol) of diethylamine were charged, and 600 ml of tetrahyrofuran was added to dissolve them, followed by cooling to −30° C. t −20° C. To the reaction mixture obtained, 77 g (0.6 mol in terms of sodium) of a sodium-naphthalene complex (sodium content: about 18% by weight) was added at the same temperature, and the reaction was further carried out at −10° C. to 0° C. for 2 hours. The reaction mixture obtained was poured into 1 liter of a saturated aqueous ammonium chloride solution, and was subjected to extraction with n-hexane. The extract obtained was washed with saturated brine, and then the solvent was distilled.

To the residue obtained, 500 ml of tetrahydrofuran and 100 ml of a tetrahydrofuran solution (1M) of tetrabutylammonium fluoride were added, and the reaction was carried out at room temperature for 1 hour. The reaction mixture obtained was poured into 1 liter of water, and was subjected to extraction with n-hexane. The extract obtained was washed with saturated brine, and then the solvent was distilled. The residue obtained was purified by silica gel column chromatography [eluting solution: n-hexane-ethyl acetate; n-hexane/ethyl acetate=4:1 (volume ratio)] to obtain 24.9 g of 3,7,11,15,19-pentamethyl-2,6-10,14-eicosatetraen-1-ol (the compound of Formula (201); Y,Z=H atoms; p=2; q=1; $R^2$=H) (yield: 68%).

What is claimed is:

1. A process for producing a all trans-form polyprenol represented by Formula (1):

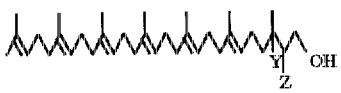

wherein Y and Z each represent a hydrogen atom, or combine to form a carbon—carbon bond;

said process comprising the steps of:

(A) subjecting a compound represented by Formula (2):

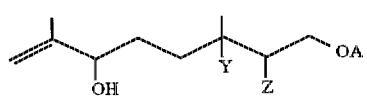

wherein Y and Z are as defined above, and A represents a protective group of the hydroxyl group;

to five-carbon lengthening reaction m-times which comprises reacting the compound of Formula (2) with 2-methyl-3,3-dimethoxy-1-butene and reducing the carbonyl group of the resulting compound, to obtain a compound represented by Formula (3):

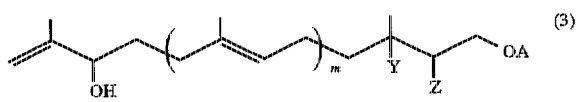

wherein Y, Z and A are as defined above, and m represents an integer of 1 to 4;

(B) subjecting the compound represented by Formula (3), to halogenation to convert it to a compound represented by Formula (4):

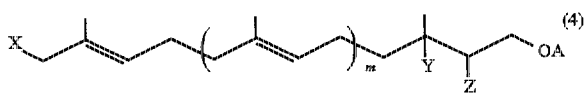

wherein Y, Z and A are as defined above, and X represents a halogen atom;

(C) allowing the compound represented by Formula (4) to react with a compound represented by Formula (5):

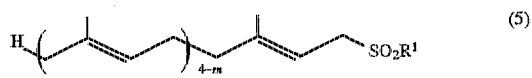

wherein m is as defined above, and $R^1$ represents an alkyl group or an aryl group;

to obtain a compound represented by Formula (6):

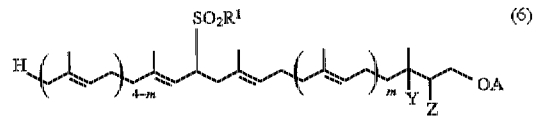

wherein Y, Z, A, m and $R^1$ are as defined above; and (D) subjecting the compound represented by Formula (6) to desulfonylation and deprotection to obtain the all trans-form polyprenol represented by Formula (1).

2. The process according to claim 1, wherein said compound represented by Formula (2), the starting material in the step (A), is obtained through the following steps (a) to (c) of:

(a) introducing a protective group A to the hydroxyl group of a compound represented by Formula (70):

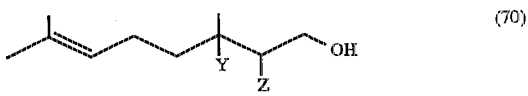

wherein Y and Z each represent a hydrogen atom, or combine to form a carbon—carbon bond;

to obtain compound represented by Formula (71):

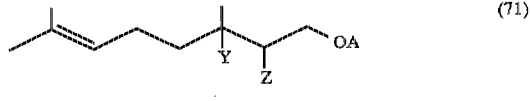

wherein Y and Z are as defined above, and A represents a protective group of the hydroxyl group;

(b) subjecting the compound represented by Formula (71) to epoxydation to obtain a compound represented by Formula (72):

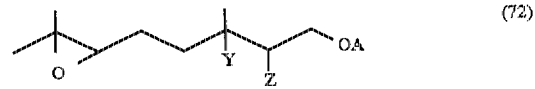

wherein A is as defined above; and
(c) rearranging the epoxy group of the compound represented by Formula (72) to an allyl alcohol to convert the compound to the compound represented by Formula (2).

3. The process according to claim 1, wherein said Y and Z each represent a hydrogen atom.

4. The process according to any one of claims 1 to 3, wherein in the step (A) the carbonyl group is reduced using an aluminum alkoxide and a secondary alcohol.

5. A process for producing a compound represented by Formula (101):

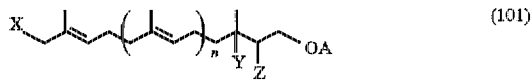

wherein X represents a halogen atom; Y and Z each represent a hydrogen atom, or combine to form a carbon—carbon bond; A represents a protective group of the hydroxyl group; and n represents an integer of 1 or more;

said process comprising the steps of:
(A') subjecting a compound represented by Formula (2):

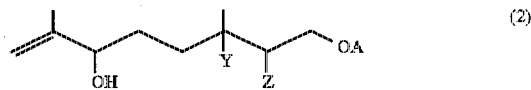

wherein Y, Z and A are as defined above;
to five-carbon lengthening reaction n-times which comprises reacting the compound of Formula (2) with 2-methyl-3,3-dimethoxy-1-butene and reducing the carbonyl group the resulting compound, to obtain a compound represented by Formula (103):

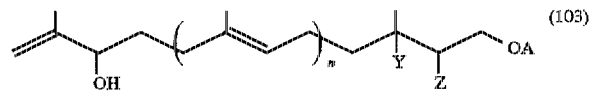

wherein Y, Z, A and n are as defined above; and
(B') subjecting the compound represented by Formula (103), to halogenation to obtain the compound represented by Formula (101).

6. The process according to claim 5, wherein said Y and Z each represent a hydrogen atom.

7. The process according to claim 5 or 6, wherein in the step (A) the carbonyl group is reduced using an aluminum alkoxide and a secondary alcohol.

8. A process comprising treating a compound represented by Formula (202):

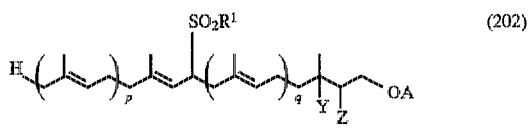

wherein p and q each represent an integer of 0 or 1 or more; Y and Z each represent a hydrogen atom, or combine to form a carbon—carbon bond; $R^1$ represents an alkyl group or an aryl group; and A represents a protective group of the hydroxyl group;

with an alkali metal and a polycyclic aromatic compound to produce a compound represented by Formula (201):

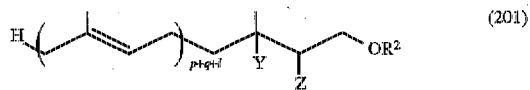

wherein p, q, Y and Z are as defined above; and $R^2$ represents a hydrogen atom or the same protective group of the hydroxyl group as that represented by A.

9. The process according to claim 8, wherein said Y and Z each represent a hydrogen atom.

* * * * *